(12) United States Patent
Bailey et al.

(10) Patent No.: US 9,339,242 B2
(45) Date of Patent: May 17, 2016

(54) SYSTEMS, METHODS, COMPONENTS, AND SOFTWARE FOR MONITORING AND NOTIFICATION OF VITAL SIGN CHANGES

(71) Applicants: Melanie Bailey, Firth, NE (US); Connie Ballew, Lincoln, NE (US); James Segermark, Gem Lake, MN (US)

(72) Inventors: Melanie Bailey, Firth, NE (US); Connie Ballew, Lincoln, NE (US); James Segermark, Gem Lake, MN (US)

(73) Assignee: Pacific Place Enterprises, LLC, Lincoln, NE (US)

( * ) Notice: Subject to any disclaimer, the term of this patent is extended or adjusted under 35 U.S.C. 154(b) by 0 days.

(21) Appl. No.: 14/246,001

(22) Filed: Apr. 4, 2014

(65) Prior Publication Data

US 2014/0221797 A1 Aug. 7, 2014

Related U.S. Application Data

(63) Continuation-in-part of application No. 12/799,243, filed on Apr. 21, 2010, now abandoned.

(60) Provisional application No. 61/934,766, filed on Feb. 1, 2014.

(51) Int. Cl.
| | |
|---|---|
| *A61B 5/00* | (2006.01) |
| *A61B 5/1455* | (2006.01) |
| *A61B 5/11* | (2006.01) |
| *G08B 21/04* | (2006.01) |

(52) U.S. Cl.
CPC ............... *A61B 5/747* (2013.01); *A61B 5/0002* (2013.01); *A61B 5/11* (2013.01); *A61B 5/14551* (2013.01); *A61B 5/14552* (2013.01); *A61B 5/6824* (2013.01); *A61B 5/6831* (2013.01); *A61B 5/743* (2013.01); *G08B 21/0453* (2013.01)

(58) Field of Classification Search
CPC ...... A61B 5/002; A61B 5/747; A61B 5/6826; A61B 5/14551; A61B 5/145; A61B 5/6831; A61B 5/0004; A61B 5/6824
See application file for complete search history.

(56) References Cited

U.S. PATENT DOCUMENTS

| | | | |
|---|---|---|---|
| 4,675,659 A | 6/1987 | Jenkins et al. | |
| 5,505,199 A | 4/1996 | Kim | |
| 6,144,303 A | 11/2000 | Federman | |
| 6,397,093 B1 | 5/2002 | Aldrich | |
| 6,553,242 B1 | 4/2003 | Sarussi | |
| 7,423,526 B2 | 9/2008 | Despotis | |
| 2002/0133067 A1 | 9/2002 | Jackson, III | |
| 2004/0111045 A1 | 6/2004 | Sullivan et al. | |
| 2005/0038326 A1 | 2/2005 | Mathur | |
| 2008/0228045 A1* | 9/2008 | Gao et al. | 600/301 |
| 2008/0266118 A1 | 10/2008 | Pierson | |

(Continued)

FOREIGN PATENT DOCUMENTS

JP 2008029590 A 2/2008

*Primary Examiner* — Steven Lim
*Assistant Examiner* — Hongmin Fan
(74) *Attorney, Agent, or Firm* — Adams Grumbles, LLP; Brittany Nanzig

(57) ABSTRACT

A system and method for monitoring and notification of injury wherein an individual wears a monitoring device, the monitoring device tracks biometric data such as blood oxygen levels, heart rate, and acceleration of the individual and sends the data to a base station, the base station analyzes the data to see if bodily changes such as decreased blood oxygen levels or significant changes in heart rate or acceleration has occurred, and the base station determines whether to sound an alarm to indicate death or severe bodily injury.

10 Claims, 27 Drawing Sheets

(56) References Cited

U.S. PATENT DOCUMENTS

| | | | |
|---|---|---|---|
| 2010/0063365 A1* | 3/2010 | Pisani et al. | 600/301 |
| 2010/0274104 A1* | 10/2010 | Khan | 600/301 |
| 2011/0021930 A1 | 1/2011 | Mazzeo et al. | |
| 2011/0112442 A1* | 5/2011 | Meger et al. | 600/595 |
| 2011/0178375 A1 | 7/2011 | Forster | |
| 2013/0072807 A1 | 3/2013 | Tran | |
| 2013/0143519 A1 | 6/2013 | Doezema | |
| 2015/0077245 A1 | 3/2015 | Kaufman et al. | |

* cited by examiner

Block Diagram of Exemplary Remote Monitoring Device Circuitry

SYSTEMS, METHODS, COMPONENTS, AND SOFTWARE FOR MONITORING AND NOTIFICATION OF VITAL SIGN CHANGES

CROSS-REFERENCE TO RELATED APPLICATION

This application incorporates by reference, and is a continuation-in-part of, U.S. Non-Provisional patent application Ser. No. 12/799,243 filed Apr. 21, 2010 titled METHOD OF PREVENTING AN INMATE FROM COMMITTING SUICIDE and also claims the benefit of U.S. Provisional Application No. 61/934,766 filed Feb. 1, 2014 titled SYSTEMS, METHODS, COMPONENTS, AND SOFTWARE FOR PREVENTING INMATE SUICIDES.

FIELD

The present invention generally relates to a method and system for monitoring at-risk individuals in confinement situations and alerting personnel to emergency situations when those individuals may attempt to harm themselves.

BACKGROUND OF THE INVENTION

People who are mentally ill are often times kept in a confined cell, room, or building and can be at risk of being injured by others or purposefully injuring themselves. Sometimes, incarcerated prisoners attempt suicide. The same is also true for patients in a psychiatric ward or hospital. The most common method of suicide attempted is strangulation by hanging. A second method of suicide attempted is cutting one's wrists. Those individuals who are believed to be a threat to themselves are usually placed on a suicide watch. This means that the individual must be at least periodically checked and preferably continuously checked to prevent the individual from committing suicide.

The requirement that the individual be continually observed results in a huge amount of expended manpower. However, if the individual is only checked or observed periodically, the individual may commit suicide between the checks or observations. In a prison situation, sudden deaths of agitated inmates in officer custody provoke allegations of misconduct by other inmates and, occasionally, unnecessary force TASER deployment. Therefore a system or method is needed that is cost-efficient and that can permit continuous monitoring of at-risk individuals, can detect an emergency situation (for example,when a person attempts to commit suicide), that sends a signal to supervising personnel, and that enables the personnel to reduce the likelihood of death and/or serious injury.

SUMMARY OF THE INVENTION

A cost-efficient method of monitoring attempted self-inflicted injury is disclosed, which comprises the steps of (1) providing to an individual an oximeter, preferably a pulse oximeter, having a Radio Frequency (RF) transmitter associated therewith, which will transmit a signal that contains data relating to the calculated oxygen saturation level of the blood of the individual, the pulse rate of the individual and the acceleration of the individual; (2) locking the oximeter and an RF transmitter onto the ankle or wrist of the individual so that the oximeter will sense and calculate the oxygen level of the individual's blood; (3) providing a monitor including an RF receiver in a location remote from the individual; (4) transmitting an RF signal containing the calculated oxygen saturation level of the individual, the pulse rate of the individual, and/or the acceleration level of the individual to the monitor so that the monitor will be alerted that the individual is attempting to inflict self-injury should the oxygen saturation level of the individual's blood drop to a certain level, should the pulse rate of the individual drop to a certain level, or should the acceleration of the individual drop to a certain level; and (5) alerting supervising personnel through an audio and/or visual alarm that the individual is possibly attempting to inflict self-injury. In summary, the system can detect vital sign changes and can alert supervising personnel, thereby helping agencies detect preventable in-custody emergencies.

Therefore the present invention provides a method of monitoring a confined individual and to alert personnel if that individual attempts to inflict self-injury. It also provides a method of monitoring a confined individual wherein a bracelet is locked onto either the wrist or ankle of the individual with the bracelet including a pulse oximeter having an RF transmitter associated therewith that transmits a signal that contains the calculated oxygen saturation level of the individual's blood to an RF receiver in a location remote from the individual with an alarm being sounded when indicated should the oxygen saturation level of the individual drop to a predetermined level, should the pulse rate of the individual drop to a predetermined level, or should the acceleration of the individual drop to a predetermined level.

The present invention also provides a method of monitoring a confined individual that eliminates the need for continually or periodically observing the individual. Additionally, the present invention provides a method of monitoring a confined individual that will also indicate and sound an alarm should the individual attempt to remove the bracelet from his or her wrist or ankle These and other systems and methods will be apparent to those skilled in the art.

BRIEF DESCRIPTION OF THE DRAWINGS

FIG. 24 illustrates a graphical user interface wherein an administrator can add or edit administrator activity.

FIG. 25 illustrates a graphical user interface wherein an administrator can view all data reports.

DETAILED DESCRIPTION

Figure 1:
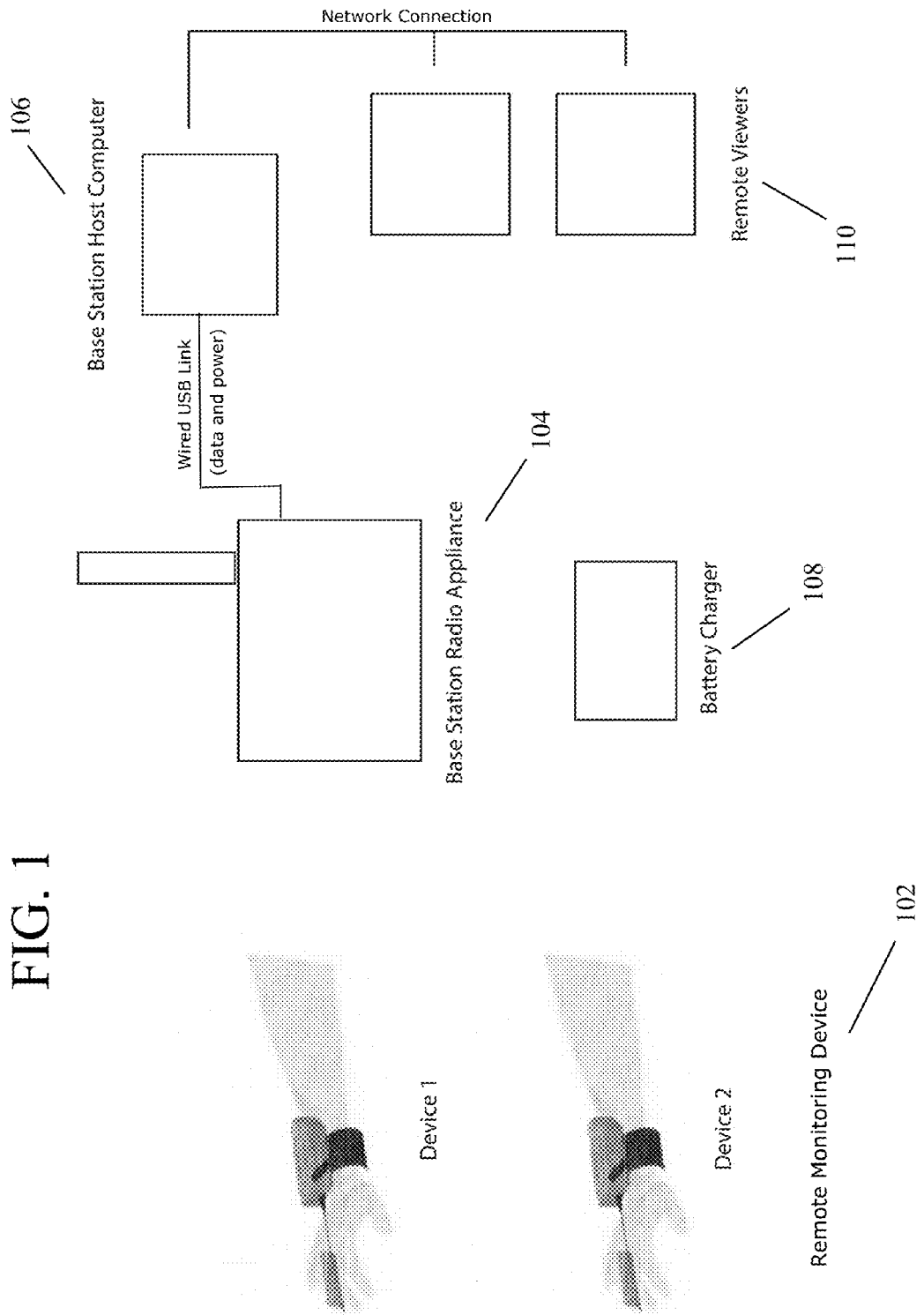
FIG. 1 illustrates the components of the system.

Various user interfaces and embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims. It is understood that various omissions and substitutions of equivalents are contemplated as circumstances may suggest or render expedient, but these are intended to cover application or embodiments without departing from the spirit or scope of the claims attached hereto. Also, it is to be understood that the phraseology and terminology used herein are for the purpose of description and should not be regarded as limiting.

Overall System Description

Generally, the disclosed invention includes a Remote Monitoring Device, Battery Charger, Base Station, and software program application. These components operate cooperatively to monitor and alert personnel when a wearer of the Remote Monitoring Device attempts to injure and/or kill him or herself.

The disclosed system can continuously monitor the blood oxygen ($SpO_2$) levels and heart rate of individuals and can alert administrators when $SpO_2$ levels or heart rate move outside of an established threshold or when tampering has been detected. The intention of the device is to detect decreased oxygenation levels in the bloodstream or changes in heart rate.

The system includes three major components: at least one Remote Monitoring Device 102 that is worn by individuals; a Base Station comprising a Base Station Radio Appliance 104 and a Base Station Host Computer 106; and a Battery Charging Station 108, as illustrated in FIG. 1. The Remote Monitoring Device 102 contains at least one pulse oximeter, which is a sensor for quantizing $SpO_2$ levels and the heart rate of the individual wearing the device. It can also detect tampering and can use a wireless data connection for bidirectional communication to a centralized monitoring system (referred to herein as the Base Station). Further, in some embodiments, it has a ruggedized mechanical design to prevent intentional or accidental damage. The Base Station includes a Host Computer 106 and Radio Appliance 104 and can support a wireless data connection for bidirectional communication from all localized Remote Monitoring Devices 102. The Base Station also contains a computer interface for communicating sensor data on a local computer station and an alarm for alerting administrators of an event. Further, the Base Station Host Computer 106 can communicate with Remote Viewers 110 through a network connection. The Battery Charging Station 108 contains an AC power-connected charging station for recharging the removable batteries of the Remote Monitoring Devices.

In one embodiment, the system can support at least twenty (20) concurrently connected Remote Monitoring Devices. The wireless data communication can operate within the 900 MHz ISM band, implement a communication protocol, and can operate over a distance of 50 meters. The wireless data communication can be robust in that it can tolerate up to 3 bits of missing or corrupted data per transmitted block without necessitating a transmission retry.

Figure 16:
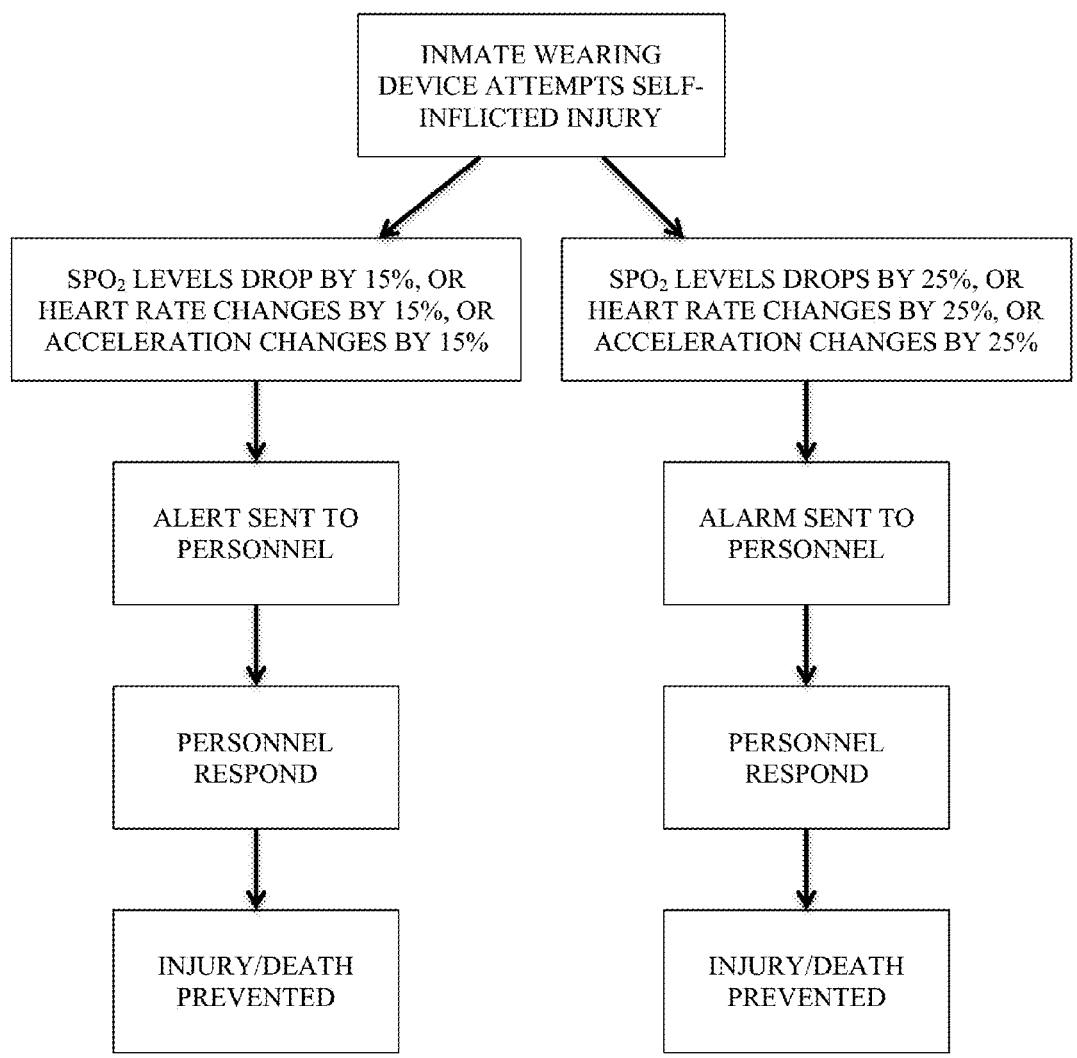
FIG. 16 is a schematic block diagram of an example method by which the system works according to one embodiment of the present invention.

As illustrated in FIG. 16, one example of using the disclosed system and method in an emergency situation includes steps wherein (1) a person in a confinement setting wears the Remote Monitoring Device (hereinafter referred to as Wearer), (2) the Wearer attempts a self-inflicted injury, (3) the Wearer's vitals, such as SpO2 levels, heart rate, or acceleration, changes by 15%, (4) the system sends an alert to personnel that the Wearer's vitals have changed by 15%, (5) the personnel respond to the alert, and (6) the Wearer's injury or death is prevented.

Also illustrated in FIG. 16, one example of using the disclosed system and method in an emergency situation includes steps wherein (1) a person in a confinement setting wears the Remote Monitoring Device (hereinafter referred to as Wearer), (2) the Wearer attempts a self-inflicted injury, (3) the Wearer's vitals, such as SpO2 levels, heart rate, or acceleration, changes by 25%, (4) the system sends an alert to personnel that the Wearer's vitals have changed by 25%, (5) the personnel respond to the alert, and (6) the Wearer's injury or death is prevented.

The system as described, while particularly useful in confinement settings, has broader capabilities. It could be modified to work in vehicles, educational institutions, office buildings and private homes. In automotive applications, for example, when individuals are being transferred to a building such as a hospital via a medical transport vehicle, or jail via a squad car, the signal can select and utilize existing communication networks already available in the area (such as mobile or other wireless data networks).

Base Station: Host Computer

The Base Station includes the host computer platform and a Radio Appliance connected to the host computer through a wired USB link. The Base Station Host Computer (BSC) and Radio Appliance (BSR) are responsible for receiving data from all localized Remote Monitoring Devices. The BSR is simply a data transfer device. Its primary responsibility is to provide the data link between the Remote Monitoring Device and the BSC. The BSC is responsible for managing the data and running the necessary monitoring algorithms on the data. The Remote Monitoring Devices communicate with the Base Station.

The BSC can be an off the shelf personal computer that includes an operating system; Ethernet network port; at least two (2) USB ports; a keyboard and mouse (or equivalent); and monitor. The exact specifications of the BSC may vary. In fact any desktop or laptop computer may be used as long as it conforms to this minimal set of specifications.

The BSC can perform user authentication using an attached finger print scanner. In lieu of passwords, a user's fingerprint can be used to identify an authorized user. The fingerprint can be registered with the application when a new user is added. In one embodiment, no significant action may be allowed to be performed prior to the user scanning their fingerprint for identification.

The BSC can activate audible and visible alarms when a Remote Monitoring Device Event is detected. The BSC software can provide the user with a visual indication of the $SpO_2$, heart rate, and motion status of each connected Remote Monitoring Device. It can also allow the user to select any of the connected Remote Monitoring Devices and view real-time status and historical reports for the current connection session. The BSC software can display a message to the user when any of the Remote Monitoring Devices has a low battery and can display a signal strength indicator for each of the connected Remote Monitoring Devices.

The BSC software can prevent the system from storing sensor data on the BSC prior to entering, at minimum, a wearer identification number, which is different from a 'user' identification number. A wearer identification number is the identification number of the person wearing the Remote Monitoring Device. This identification is needed to map the data to the respective person. The BSC can request a current list of node serial numbers visible to the BSR when required to assign a radio to a wearer. The BSC can request a data packet from each authenticated node at a periodic rate.

The BSC can initialize the fingerprint sensor through its API function calls upon initial startup. The BSC can catalog, in an encrypted file on the computer, all user info with the clearance to user the fingerprint sensor for authentication. It can allow users with clearance to be suspended from the active list.

Battery replacement activity can be limited to situations when the Wearer is in an inactive state. Similarly, the pulse oximeter replacement activity can be limited to situations when the Wearer is in an inactive state. In an inactive state, the Wearer is not being monitored, so the removal of the battery or pulse oximeter does not cause an alert.

The BSC can, in one embodiment, only initiate sound alert 'chirps' at the Base Station. However, in one embodiment, it can initiate alert 'chirps' and alarm sounds at the Base Station and/or the Remote Monitoring Device. For example, the BSC can initiate an alert chirp if the $SpO_2$ level drops by the configured alert percentage from the baseline, which is a configured parameter for each given wearer. It can also initiate a chirp alert if a Remote Monitoring Device reports a heart rate below the configured alert heart rate or if a Remote Monitoring Device reports wearer movement below the configured stillness threshold continuously for the configured stillness alert duration. It can initiate an alarm sound if a Remote Monitoring Device reports a heart rate below the configured alarm heart rate, if a Remote Monitoring Device reports that the $SpO_2$ levels dropped by a configured alarm percentage, or if a Remote Monitoring Device reports wearer movement below the configured stillness threshold continuously for the configured stillness alarm condition.

The BSC can allow the user to silence an alarm on the Base Station only. The BSC should not allow the user to silence an alarm on the Remote Monitoring Device once it has been initiated. The alarm condition at the Remote Monitoring Device, in one embodiment, must be silenced by direct operator/user intervention at the Remote Monitoring Device.

The BSC can have a default baseline in the software. It can also be modified by allowing a baseline reading to be taken by the Remote Monitoring Device. There may be a GUI requirement and Remote Monitoring Device requirement to reflect this. In addition, the configured alert percentage has a software default of 15%. The BSC can initiate an alarm sound if the $SpO_2$, heart rate, or movement levels drop by the configured alarm percentage from the baseline, which has a default in the software of 25%. However, the configured alert and configured alarm percentages may be modified through the GUI.

This section lists all of the requirements associated with the GUI for the BSC. Its intent is to ensure general functionality is provided by the GUI. Specific screen elements and function are defined in the GUI Functional Specification.

Figure 18:
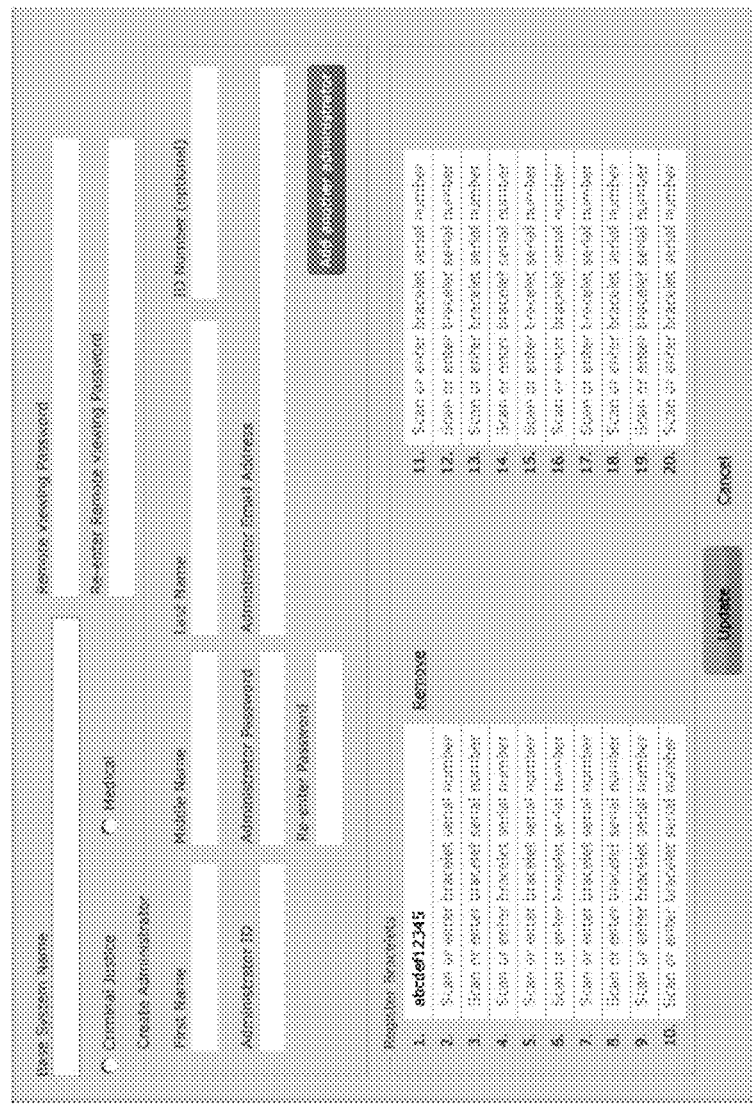
FIG. 18 illustrates a graphical user interface of the setup screen.

The BSC User Interface (UI) Setup Screen can permit the user to choose between permanently storing and discarding any changes made to any fields or selections. The Setup Screen fields, as illustrated in FIG. 18, can include information such as, but not limited to, the Base System Name and identity and authentication information for a single Administrator. The Administrator identity and authentication information can include information such as, but not limited to, first, middle and last name, ID Number, Administrator Email Address, Administrator User ID and Administrator Password. The Setup Screen, in one embodiment, shall not allow exit until at least one System Administrator and the System Name is entered.

In one embodiment, the BSC Graphical User Interface (GUI) can show, on monitoring screen, the status of each measured vital sign and the status of each battery in a Remote Monitoring Device. In one embodiment, the GUI shall monitor and display at least twenty (20) watches on the screen at a time. The BSC can maintain data of monitored people in a de-identified state, with the option to add personal identification. 'De-identified' means that the GUI will not force a user to enter the name of the person wearing the Remote Monitoring Device; only an identification number will be required. The option to enter additional information, such as the persons' name, will be allowed.

The GUI supports a variety of actions. For example, a user can be disabled without the loss of their history; Administrators can edit users' permission levels; and new users can be set up in the system using fingerprint sensor ID. Additionally, the GUI can automatically override a minimized screen if an alert or code is detected and not allow it to be cleared until staff responds, and it can allow a baseline $SpO_2$ level to be recorded from a Remote Monitoring Device. The GUI can allow the following algorithm variable/thresholds to be configured at the system level: $SpO_2$ Alert Percentage; $SpO_2$ Alarm Percentage; Heart Rate Alert Percentage; Hear Rate Alarm Percentage; Motionless Alert Time.

Figure 19:
FIG. 19 illustrates a graphical user interface wherein the home screen shows an alert for one remote monitoring device wearer.
Figure 21:
FIG. 21 illustrates a graphical user interface wherein the home screen shows an alert for one remote monitoring device wearer.
Figure 23:
FIG. 23 illustrates a graphical user interface wherein the home screen shows an alert for one remote monitoring device wearer.

The BSC UI Home Screen can display the Base System Name, status information for at least twenty (20) connected Remote Monitoring Devices simultaneously, and each actively monitored Remote Monitoring Device Wearer with the Wearer's identification number and Remote Monitoring Device serial number, as illustrated in FIGS. 19, 21, and 23. The Home Screen can also provide a link to the Administrator Login screen. Within the Home Screen, each Remote Monitoring Device can indicate whether it needs to be Set Up with user information, as illustrated in FIG. 19, has a low battery, as illustrated in FIG. 21, or is sending an alert to the Base Station, as illustrated in FIG. 23.

The Home Screen can generate an individually identifiable, time-stamped report for each Alert/Alarm event. Additionally, the Home Screen can display a current status box shall for each Remote Monitoring Device Wearer that quickly indicates overall alert/alarm status. The status box can have border colors as follows: nominal condition is grey; mouse pointer click within box is highlighted (e.g., white); alert condition is flashing yellow; alarm condition is flashing red. Each status box can also display individual icons representing the following information: person photo thumbnail; heart rate change status; $SpO_2$ change status; motion change status; battery life status; signal strength status; and reports generated, as illustrated in FIGS. 19, 21, and 23.

Figure 22:
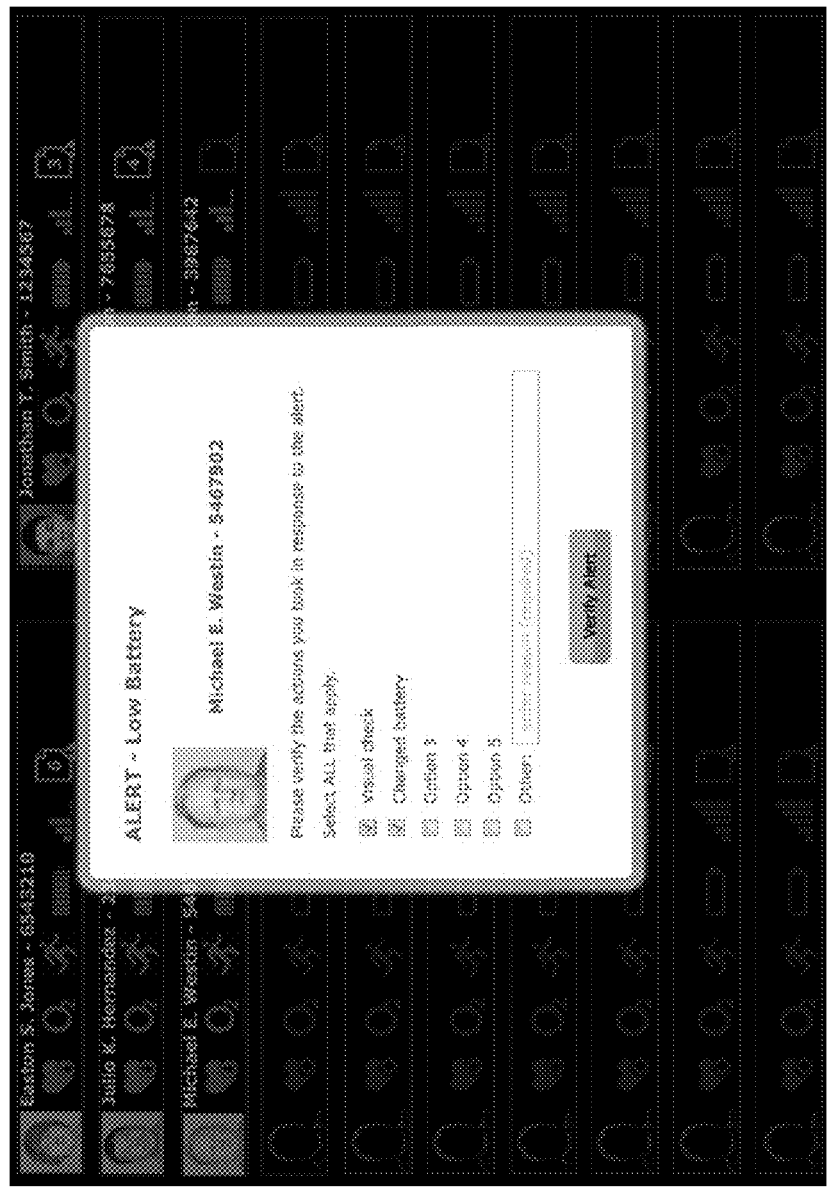
FIG. 22 illustrates a graphical user interface wherein a status box displays a concise message containing instructions associated with the most current alert condition.

If there is a current or recent alert condition, the status box can display a concise Alert Text message containing instructions associated with the most current alert condition, as illustrated in FIG. 22. Otherwise, if no alert condition has recently occurred or is currently occurring, the status box is blank. Once an alarm or alert has occurred and a new report has been created, the status box "reports generated" icon can appear and show the number of total reports. The status box icons can, for alert/alarm conditions, change appearance to indicate increasing, decreasing, and static conditions in regard to heart rate change, $SpO_2$ change, and motion change.

Figure 20:
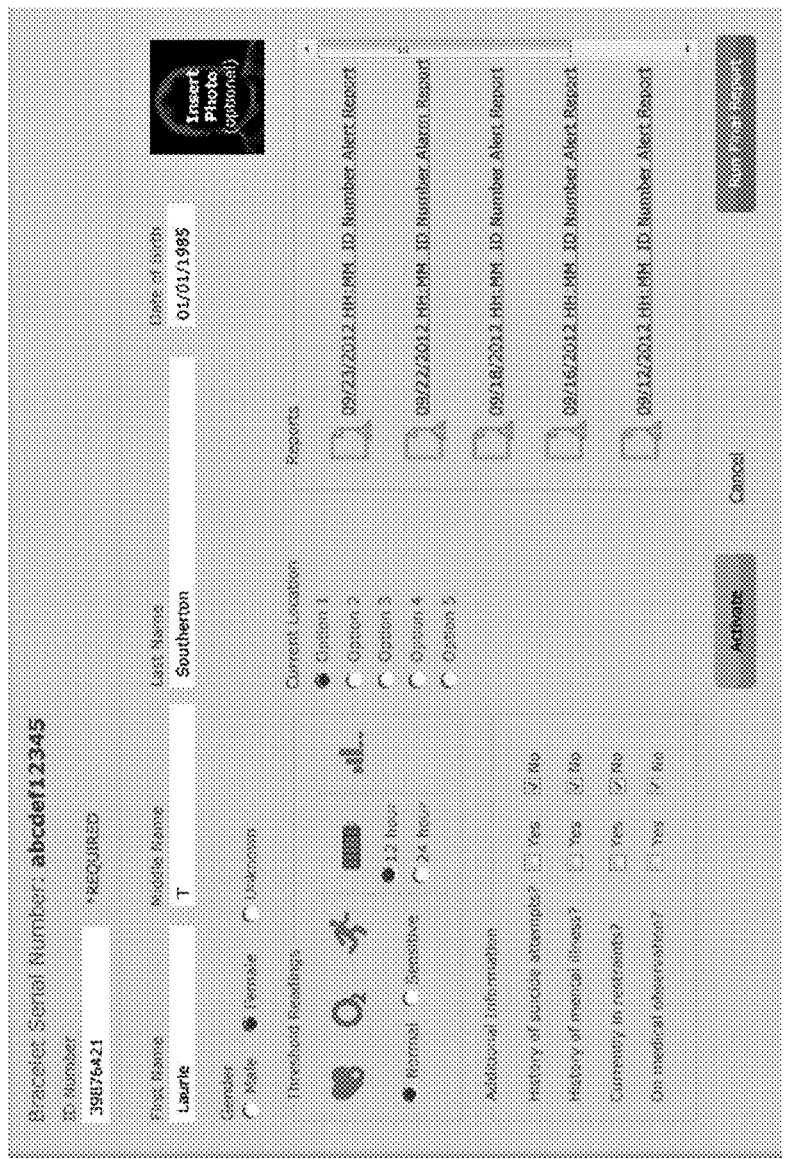
FIG. 20 illustrates a graphical user interface wherein an administrator can enter information about a person wearing a remote monitoring device.

The Home Screen can respond to a user clicking anywhere within a status box by prompting the user for login credentials. Only a valid login may allow a user to do one of the activities described below. If the condition is nominal, clicking anywhere within a status box and inserting proper credentials may permit the user to, for example, display, edit, or report related person information via the Person Detail Screen, as illustrated in FIG. 20. If the condition is alert/alarm, clicking anywhere within a status box and inserting proper credentials may permit the user to, for example, verify or report the reason for the alert/alarm via the Alert/Alarm Verified Dialog, as illustrated in FIG. 22.

In one embodiment, only users with Person Setup/Edit permissions may be allowed to access the BSC UI Wearer Setup Screen, with permission failure indicated by a corresponding message. The Wearer Setup Screen can display the base system name and the Remote Monitoring Device serial number associated with the respective person, as illustrated in FIG. 20.

In general, the Wearer Setup Screen can permit the user to choose between permanently storing and discarding any changes made to fields or selections through the use of a corresponding action button. Within the Wearer Setup Screen, as illustrated in FIG. 20, the user can input information such as, but not limited to, person info, thresholds, location, and medical history. In addition to inputting information, a user can take certain actions within the program. These actions include, but are not limited to, viewing reports, initiating manual battery replacement, reporting battery replacement with a time and date stamp, and initiating pulse oximeter replacement. The Wearer Setup Screen can provide a means to Activate (turn on monitoring) and Deactivate (turn off monitoring for the wearer).

As stated above, the Wearer Setup Screen, as illustrated in FIG. 20, can provide means to display, edit, or select person information such as, but not limited to, first name, middle name, last name, person ID number, date of birth, gender, and photo. The Wearer Setup Screen can provide means to select between normal and sensitive thresholds used to determine normal/alert/alarm levels for heart rate, $SpO_2$, and/or motion changes, the default of which is a normal threshold. The Wearer Setup Screen can provide means for the user to specify person location as a selection from a location list. It can also allow the user the option of providing answers for the following questions about the corresponding person: history of self-inflicted bodily harm/suicide attempts, history of mental illness, currently in restraints, and on medical observation.

Further, the Wearer Setup Screen can provide means to view the reports for a Wearer. Sometimes the reports are in the form of a Summary Report File formatted as a comma-separated-values (CSV) file containing all reports generated for the Wearer. The Wearer Setup Screen can also provide means to initiate a manual battery replacement action and it can provide means to initiate a pulse oximeter replacement action. The Wearer Setup Screen can generate a report indicating the battery replacement action with a time and date stamp.

The BSC Insert Photo Dialog can provide means to select, replace, and delete a person. In one embodiment, it can support JPEG, PNG, and GIF image file formats. The Photo Dialog can auto-scale images as required for efficient storage while preserving aspect ratio so that person identification photos are not stretched or otherwise distorted.

Only approved users with stored fingerprint data may be able to access the BSC UI Alert/Alarm Verified Dialog, with authentication failure indicated by a corresponding message. The Alert/Alarm Verified Dialog may uniquely identify itself as an Alert or Alarm and can display text that describes the nature of the Alert or Alarm condition, as illustrated in FIG. 22. The Alert/Alarm Verified Dialog can display the following person identity information: thumbnail photo, person name, and person ID number.

As illustrated in FIG. 22, the Alert/Alarm Verified Dialog can also provide means for the user to specify all actions taken in response to the Alert/Alarm condition, which includes a multiple checklist of common associated responses as well as an "Other" option to provide for manual entry of a custom action description. In one embodiment, the Alert/Alarm Verified Dialog may require selection of at least one action, and subsequent pressing of a "verify" button, before allowing exit.

After an alert or alarm, the Alert/Alarm Verified Dialog may append details to the current alert/alarm report such as, but not limited to, authenticated user's ID number and timestamp indicating time of Alert/Alarm acknowledgement. Further, it can notify the user that an associated report is available.

The BSC UI Administrator Detail Screen, as illustrated in FIGS. 24 through 27, may, in one embodiment, only be accessed through an authenticated administrator login. It can display the base system name and can provide access to administrative activities such as, but not limited to, add/edit users; view all data reports; edit/setup administrators; monitor parameters; and system setup. The Administrator Detail Screen can be closed and/or exited by logging out.

Figure 24:
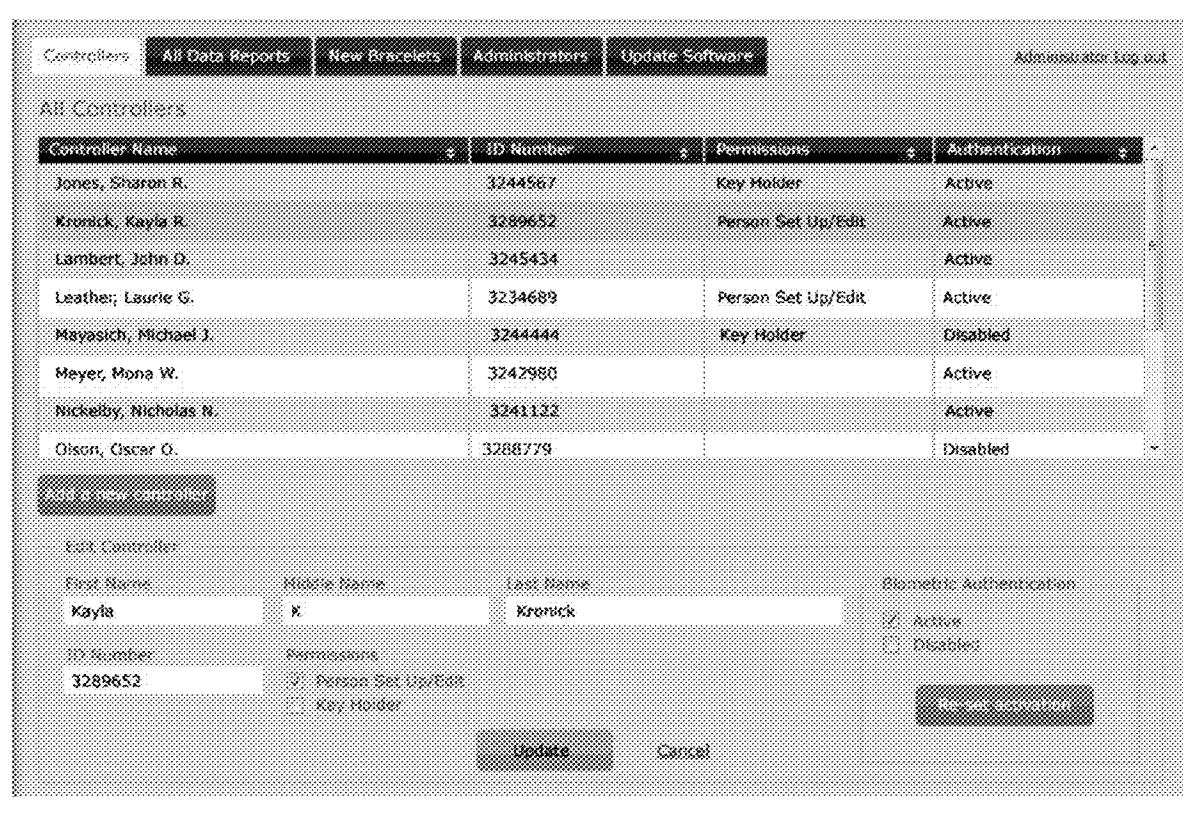

Within the Administrator Detail Screen, the Add/Edit Users Activity, as illustrated in FIG. 24, can provide means to display a list of administrators that includes fields such as, but not limited to, user name, ID number, access/usage permissions, and biometric authentication status, some of which may be sortable. The Add/Edit Users Activity can provide the means to add a new user or modify current user records by selecting a user from the list for display, edit, or deletion.

After selecting a user from the list, the screen can display and permit the user to edit user details such as, but not limited to, first name; middle name; last name; ID number; access/usage permissions; and biometric authentication status, as illustrated in FIG. 24. The access/usage permissions include person setup/edit, which allows access to person detail screen, and key holder, which allows access to alert/alarm verified dialog, one or both of which can be selected. The biometric authentication status options include active and disabled. In active state, this user is allowed to log in and this shall not be selectable (shall be greyed out) until biometric data has been captured. In disabled state, this user is prevented from logging in (default state).

An action button (e.g., "Re-Set Authentication") can also be on this screen that, when selected, initiates biometric capture. This can be used for both initialization and replacement of user biometric data. The Add/Edit Users Activity on the Administrator Detail Screen can allow the user to choose between permanently storing and discarding all changes made to user data fields.

Figure 25:
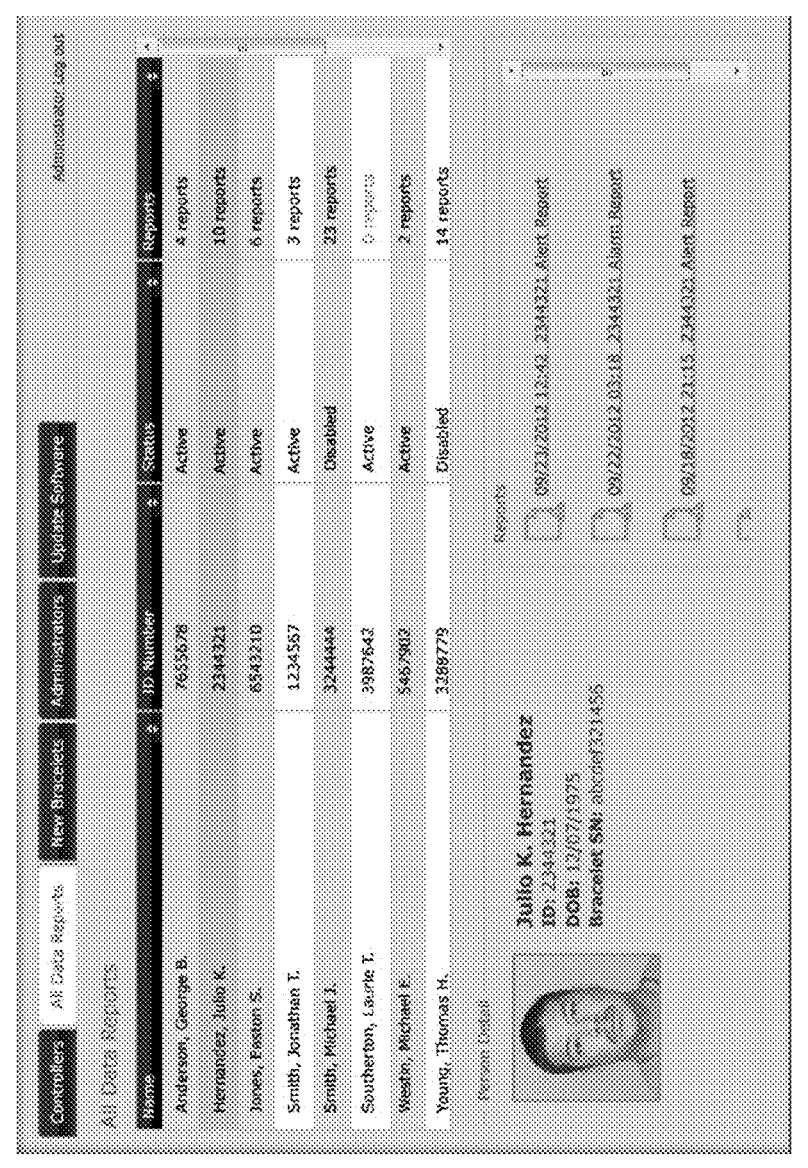

Within the Administrator Detail Screen, a user can view all data reports, as illustrated in FIG. 25. The user interface can provide means to display a list of person report records that includes fields such as, but not limited to, person name; person ID number; Remote Monitoring Device activation status; and total reports for this person, some of which may be sortable. The Data Reports Activity UI can permit selection of an individual person report record, which can then display a person's photo, name, ID number, date of birth, Remote Monitoring Device serial number, and a list of this person's reports, which can be individually selected by the user. The Data Reports Activity UI can permit an administrator to edit settings for any administrator.

The Administrator Detail Screen can permit an Administrator to create and maintain a text list of unique labels for all Remote Monitoring Device use locations. The Person Detail Screen can allow the user to select a person's current location from this list.

Figure 27:
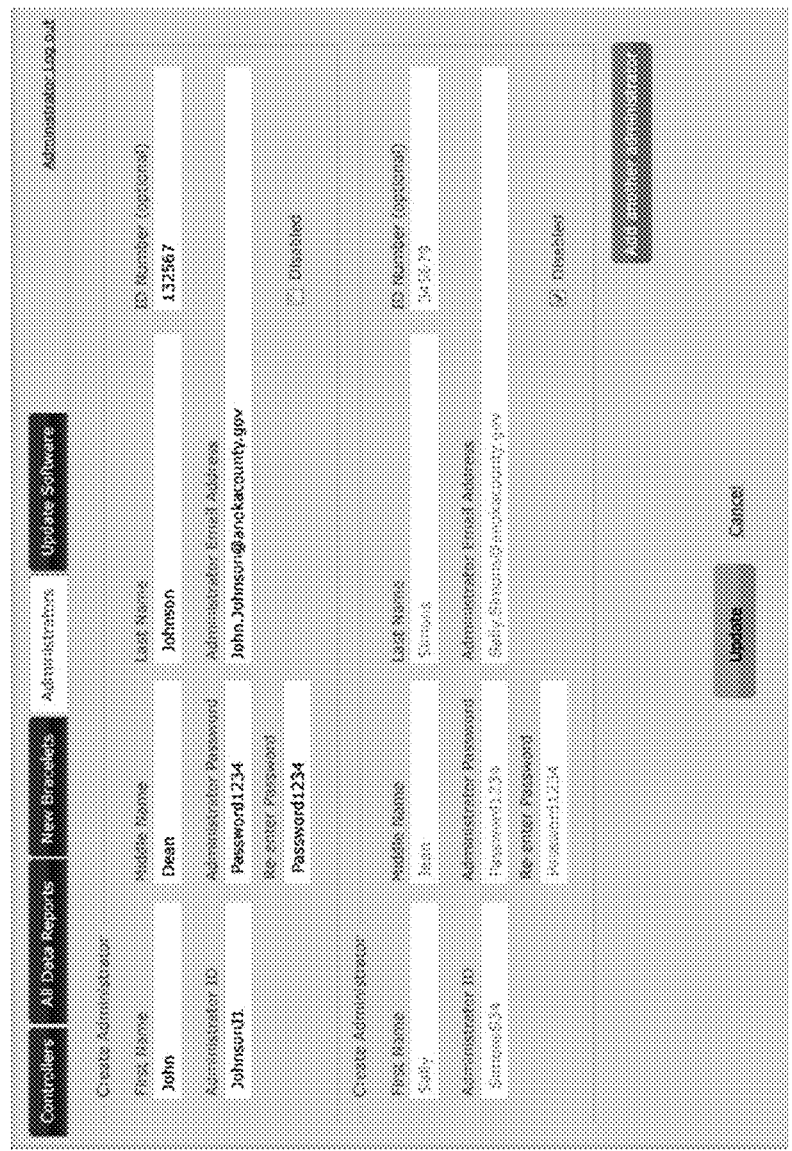
FIG. 27 illustrates a graphical user interface wherein an administrator can edit or setup another administrator.

The Administrator Detail Screen also permits an Administrator to edit and setup one or more administrators, as illustrated in FIG. 27. Within this edit and setup screen, an Administrator can enter information such as, but not limited to, new Administrator first name, middle name, last name, ID number, Administrator ID, Password, and email address. This screen can permit the Administrator to choose between permanently storing and discarding any changes made to fields through the use of a corresponding "update" or "cancel" action button.

In one embodiment, the BSC UI Administrator Login Dialog can require an Administrator ID and Password for access authentication. In the event of authentication failure, the Administrator Login Dialog can display text indicating that the Administrator ID/Password combination is invalid. The Administrator Login Dialog can provide means to accommodate a forgotten password by allowing an administrator to login with a fingerprint scan.

The BSC UI User Login Dialog can prompt the user to place his or her finger on a fingerprint sensor for proper biometric verification, and can provide a progress bar, or similar animated graphic, to indicate that the fingerprint sensor is actively awaiting finger placement. The User Login Dialog can provide a means to cancel the login and any biometric verification in progress and may time out after a period of thirty (30) seconds of no interaction from the user, having the same result as canceling the login. In the event verification is unsuccessful, the User Login Dialog can display the cause of failure and prompt the user to retry. It can allow the user to retry verification a predetermined number of times before prompting that the login was unsuccessful and instructing the user to contact an administrator.

The BSC UI Alert/Alarm Report can include the following fields: person ID number; Remote Monitoring Device serial number; designation of "Alert" or "Alarm"; timestamp of Alert/Alarm generation; reason(s) for Alert/Alarm generation (including Home Screen Status Text message); timestamp of Alert/Alarm acknowledgement; user ID number of authenticated Alert/Alarm acknowledger; and action(s) taken in order to clear Alert/Alarm, including any "Other" text.

Base Station: Radio Appliance

As described above, the Base Station Radio Appliance (BSR) is a data transfer device. Its primary responsibility is to provide the data link between the Remote Monitoring Devices and the BSC.

In one embodiment, the BSR can have a single omnidirectional antenna. It can be powered via its USB connection to the BSC and can be on and fully functioning as long as power is available. The BSR USB connection can be a standard USB Target connection. The BSR may be able to receive data from at least twenty (20) Remote Monitoring Devices simultaneously. Additionally, the BSR can provide a biometric fingerprint scanner that allows for user authentication.

The BSR can be capable of generating an audible sound with a frequency between 500 Hz and 3.5 KHz, and a sound pressure of at least 90 dBA at a distance of 10 centimeters. The BSR software can allow for the activation/deactivation of the alarm as well as the chirp function. However, the audible alarm should power-up default to the "inactive" state and maintain its current state until another alarm command is received or power is lost. The BSR audible alarm "chirp" state can be a repeated patter of ON for 250 ms and OFF for 4750 ms.

The BSR can send an Activate message and Deactivate message to each individual detected Remote Monitoring Device and can generate an audible chirp alert when communication with any of the activated Remote Monitoring Devices is lost or the data has lost integrity.

Remote Monitoring Device

Figure 14:
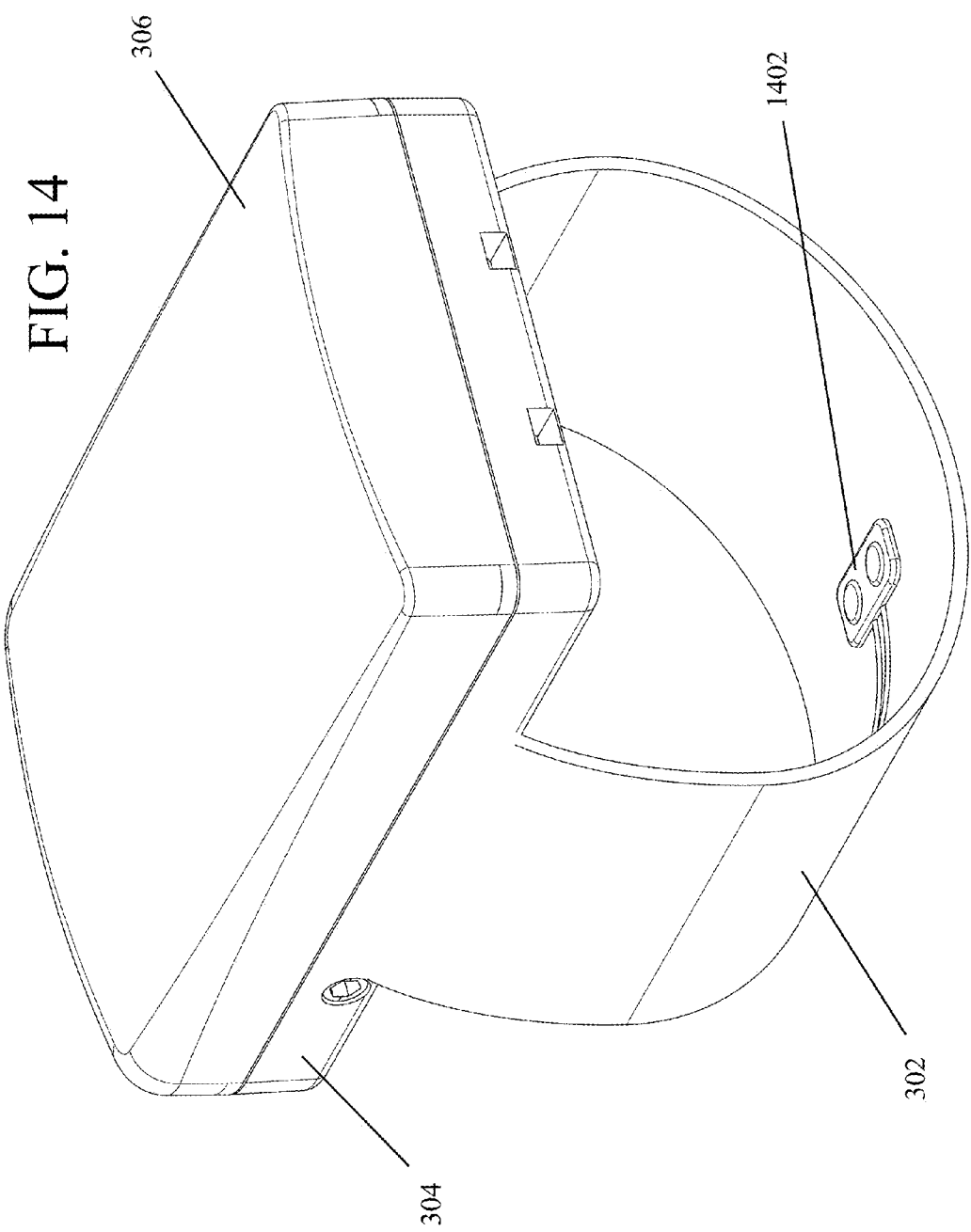
FIG. 14 illustrates a perspective back view of a remote monitoring device without a finger-based pulse oximeter attached.
Figure 15:
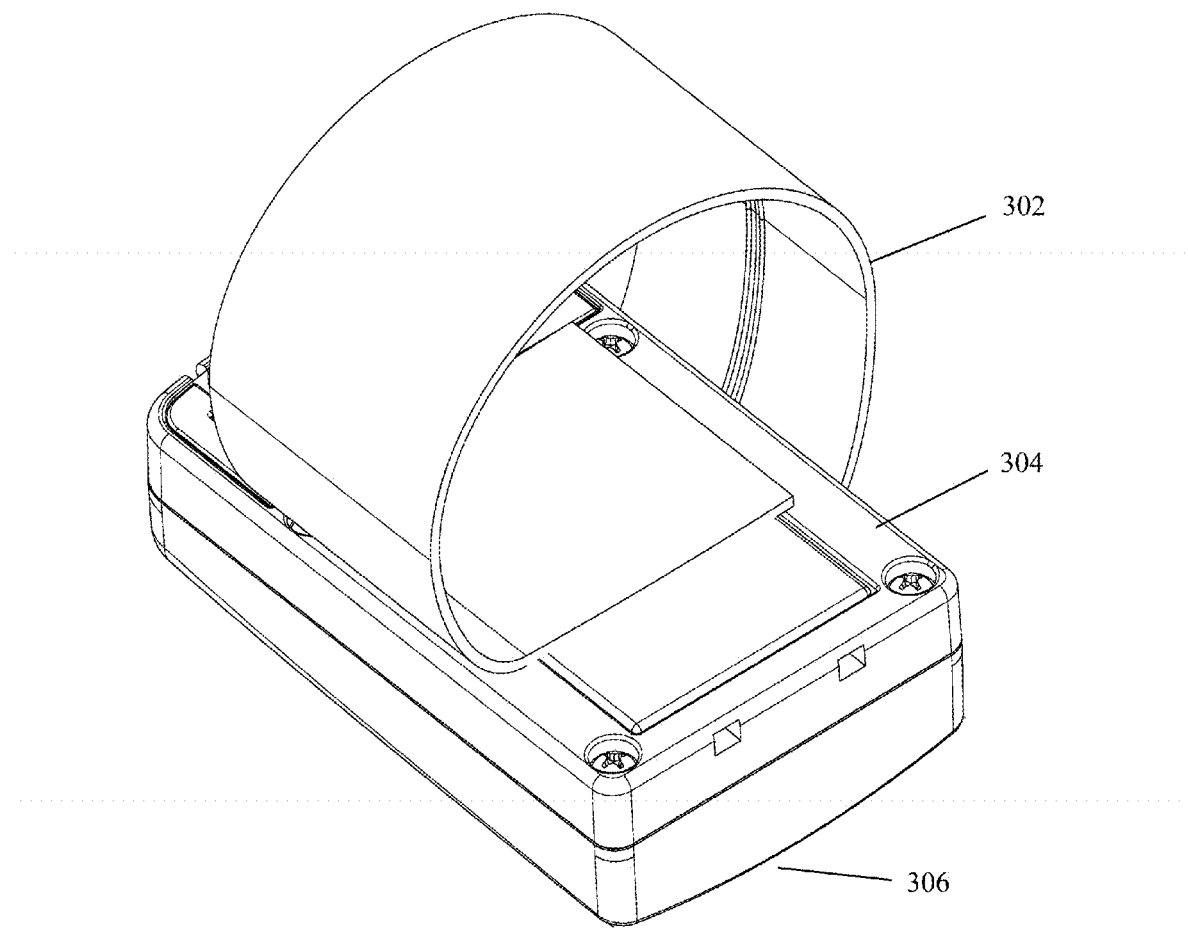
FIG. 15 illustrates a perspective bottom view of a remote monitoring device wherein the pulse oximeter is attached to the inside of the wrist strap.

In one embodiment, the Remote Monitoring Device includes a wrist strap, interface, keyhole, pulse oximeter, speaker, cable, processor, wireless transceiver, batter, and 3-axis accelerometer. FIGS. 3 through 8 illustrate one embodiment of the Remote Monitoring Device wherein the device can use, but is disconnected from, an external pulse oximeter. FIGS. 9 through 13 illustrate one embodiment of the Remote Monitoring Device wherein the device is connected to an external pulse oximeter. FIGS. 14 and 15 illustrate one embodiment of the Remote Monitoring Device wherein the pulse oximeter is integrated into the wrist strap.

Figure 8:
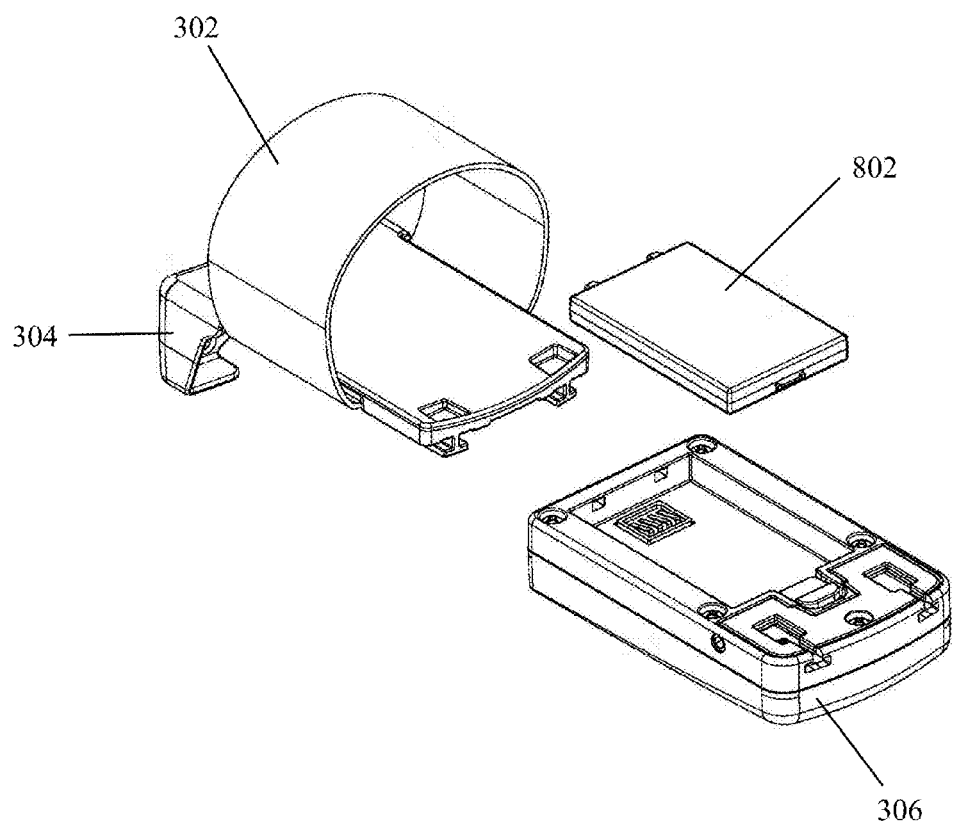
FIG. 8 illustrates a perspective bottom and side view of a remote monitoring device without a finger-based pulse oximeter attached and with the battery removed.
Figure 9:
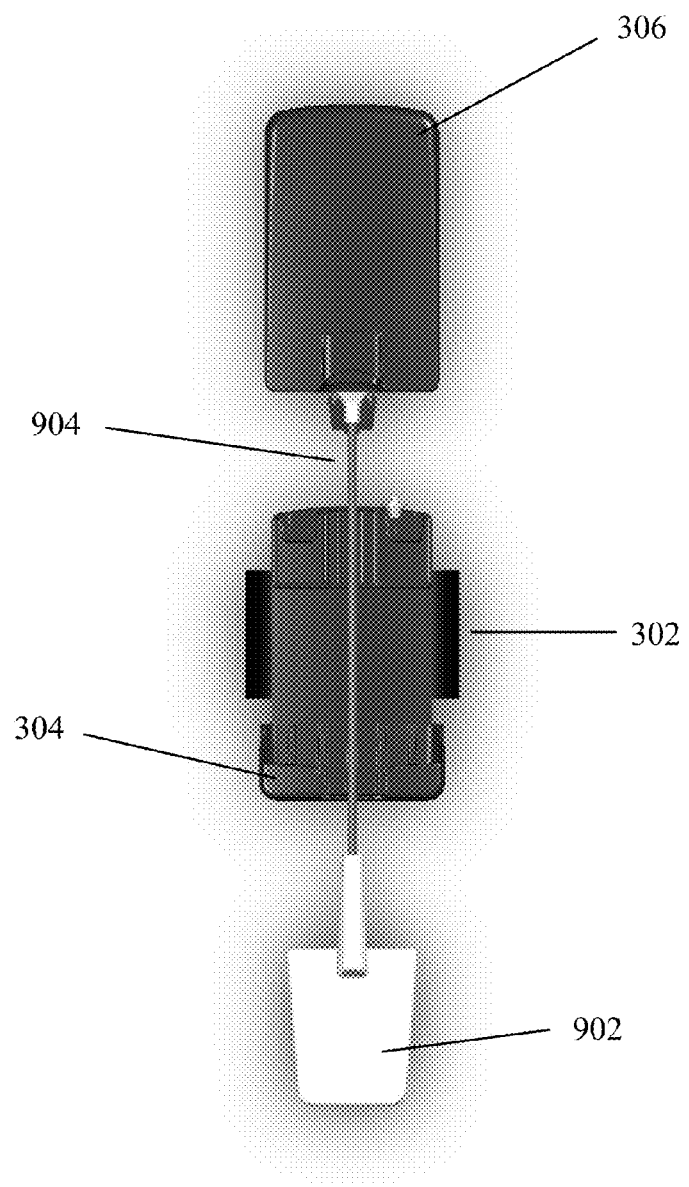
FIG. 9 illustrates a top down view of a remote monitoring device with a finger-based pulse oximeter attached.
Figure 10:
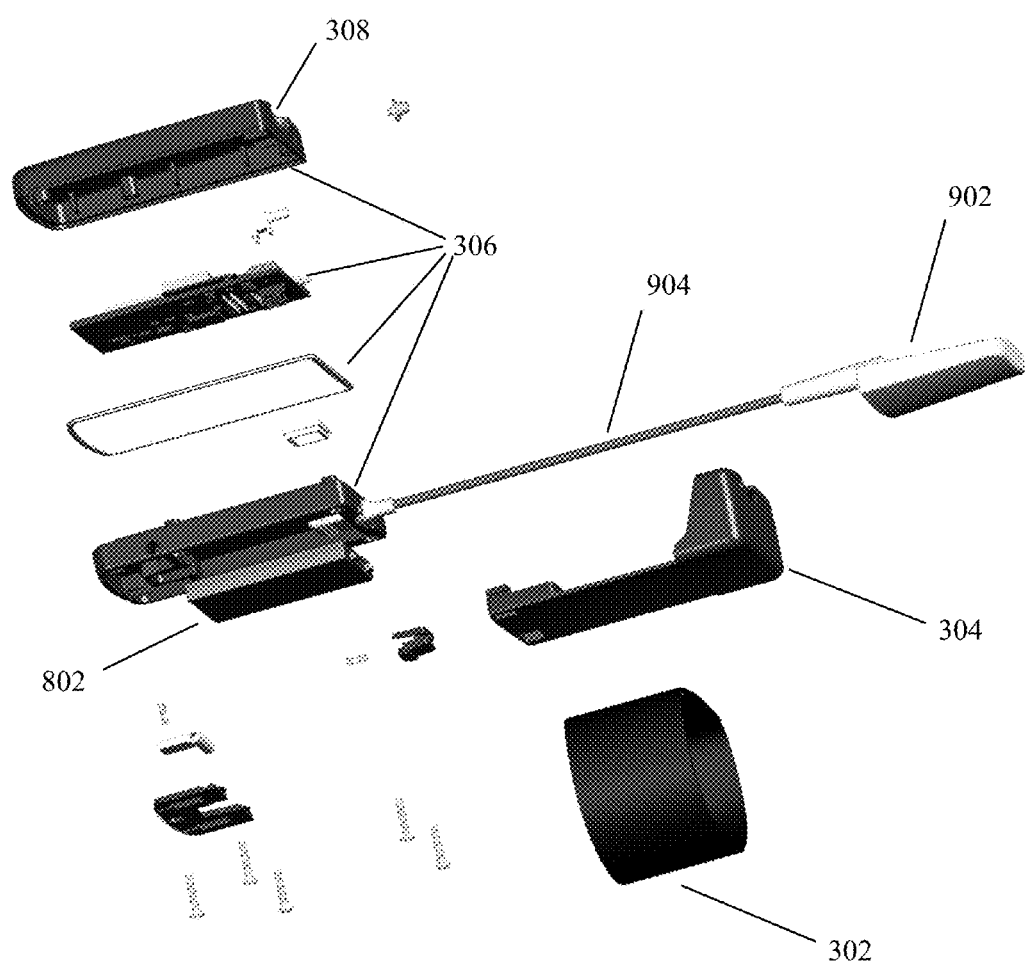
FIG. 10 illustrates an exploded bottom-up view of a remote monitoring device with a finger-based pulse oximeter attached.
Figure 11:
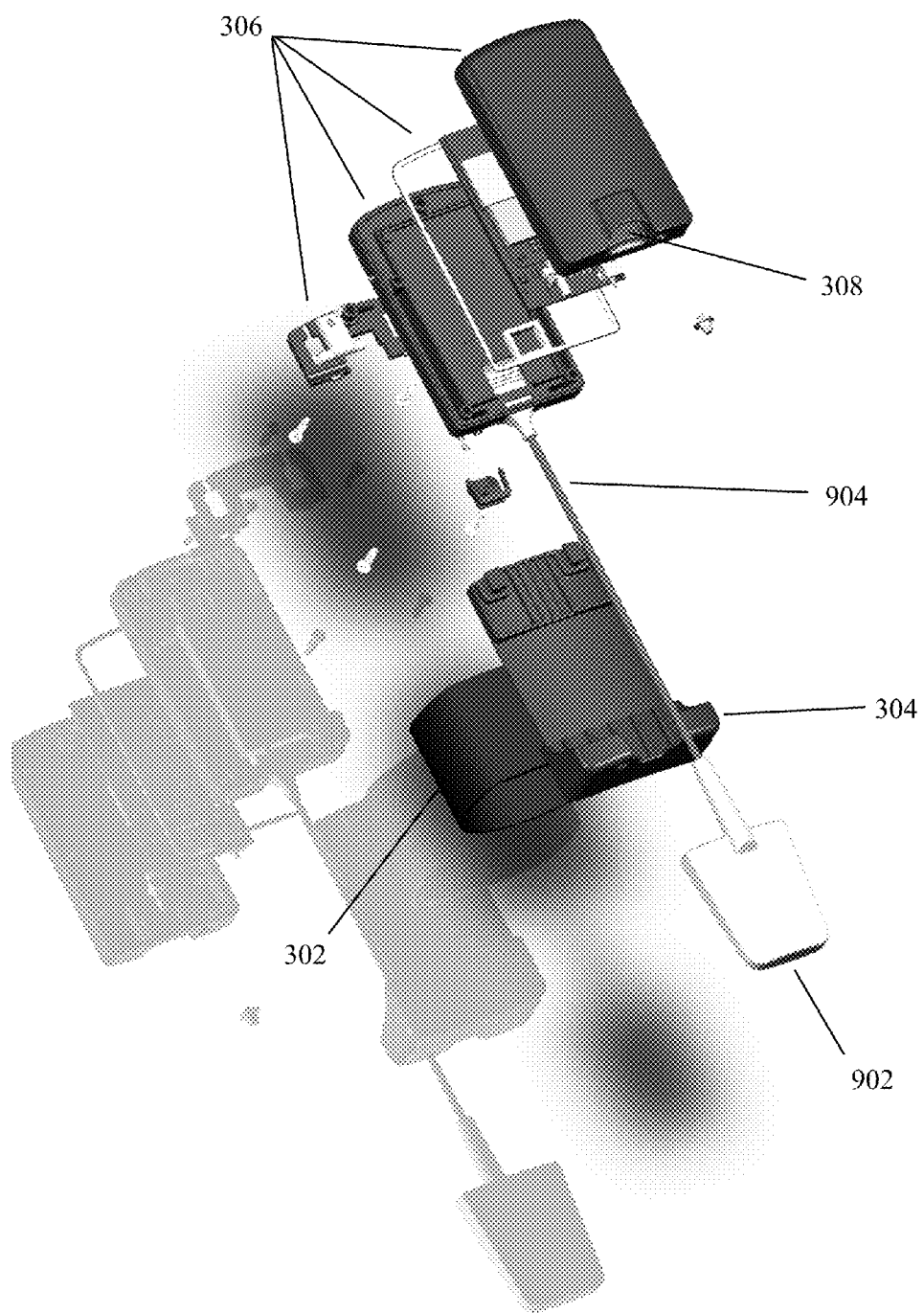
FIG. 11 illustrates an exploded top-down view of a remote monitoring device with a finger-based pulse oximeter attached.
Figure 12:
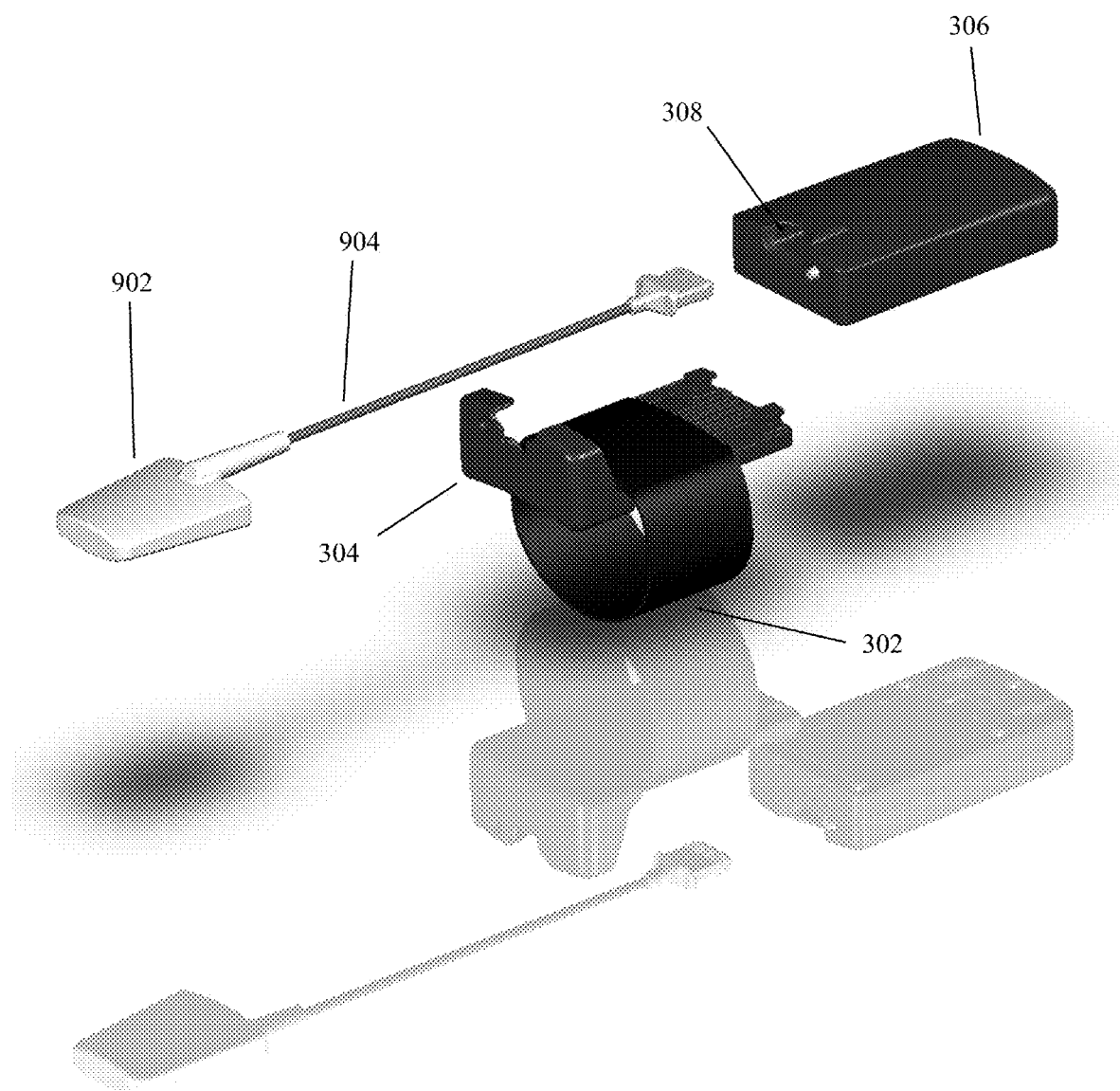
FIG. 12 illustrates a perspective side view of a remote monitoring device, finger-based pulse oximeter, and wrist strap that are all separated.
Figure 13:
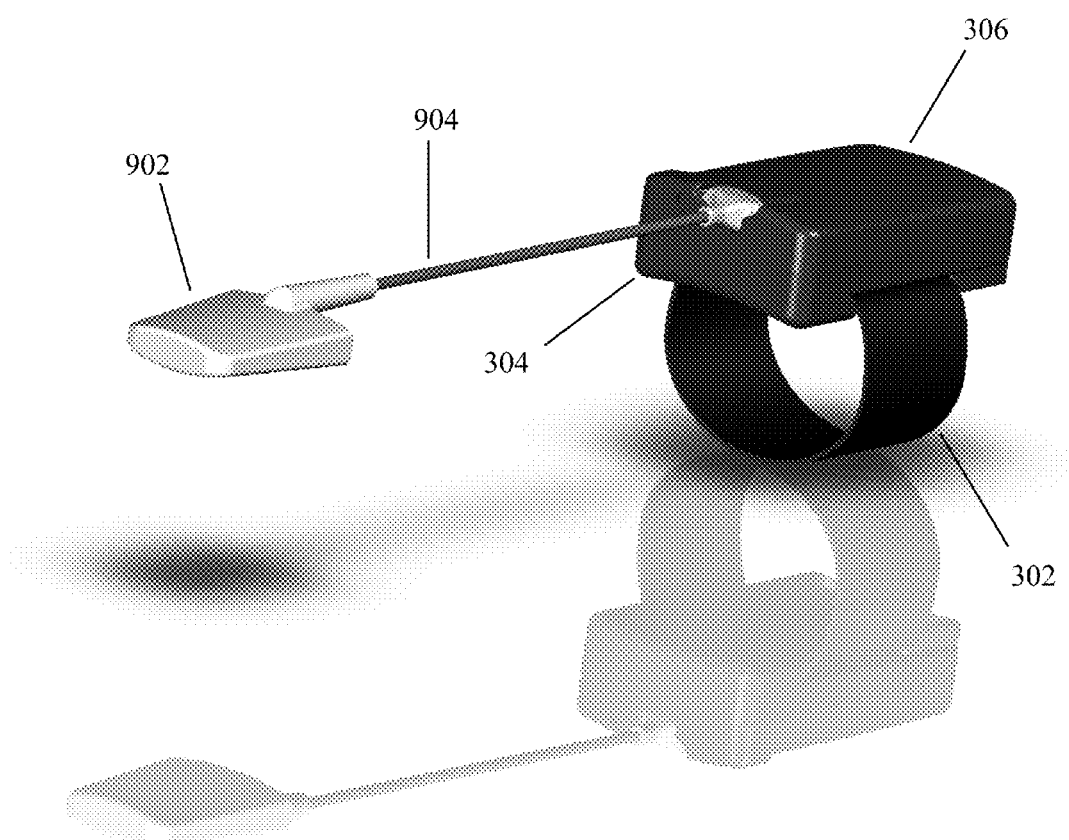
FIG. 13 illustrates a perspective side view of a remote monitoring device with a finger-based pulse oximeter attached.

A rechargeable battery 802 that is removable from the Remote Monitoring Device, as illustrated in FIG. 8, can power the Remote Monitoring Device. The Remote Monitoring Device's rechargeable battery 802 can be protected against over-heating, charge current exceeding the battery's maximum charge rate, charge voltage exceeding the battery's maximum charge voltage, discharge current exceeding the battery's safe rate, and discharge beyond the battery's minimum discharge voltage. With a full charge, the rechargeable battery 802 is intended to operate continuously, under nominal functional conditions, for a minimum of 24 hours.

Figure 6:
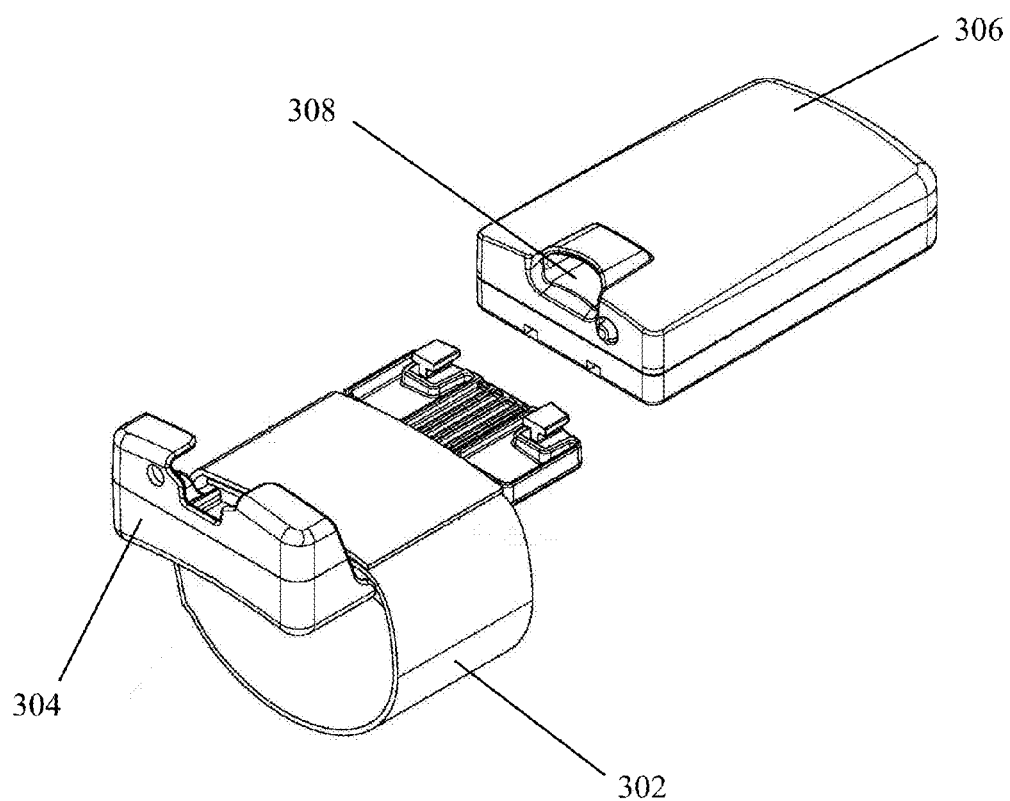
FIG. 6 illustrates a perspective top view of a remote monitoring device without a finger-based pulse oximeter attached.
Figure 7:
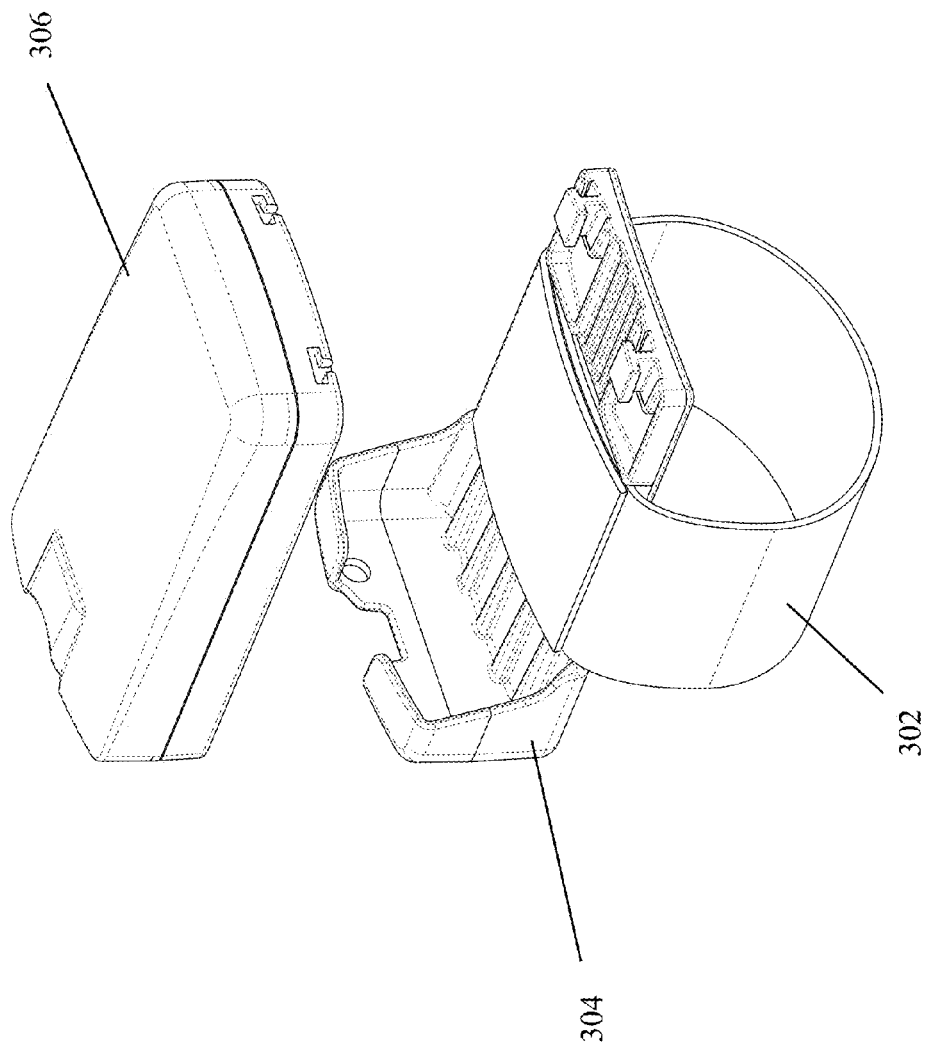
FIG. 7 illustrates a perspective back view of a remote monitoring device without a finger-based pulse oximeter attached.

The Remote Monitoring Device can be detachable from its wrist strap 302, as illustrated in FIG. 6, and the rechargeable battery 802 is removable when the Remote Monitoring Device is detached from its wrist strap 302. Additionally, the wrist strap 302 is adjustable in order to fit wearers' wrists of varying circumferences. The wrist strap 302 may be adjustable because it is made of a hook and loop strap (for example, Velcro). In one embodiment, the means for adjusting the wrist strap 302 are inside the wrist-mounted enclosure 204, as illustrated in FIG. 6. The end edge of the wrist strap 302 is concealed between the cradle 304 and the transceiver module 306 to inhibit removal by a person wearing the device. To remove the wrist-mounted enclosure 204 from the wrist strap 302 of the Wearer, the wrist-mounted enclosure 204 may require the use of a key. In one embodiment, the Remote Monitoring Device's pulse oximeter 902, which is a sensor that detects $SpO_2$ levels and pulse, is a device that can be affixed around any of the pinky, ring, middle, or index fingers, as illustrated in FIGS. 9 through 13. As illustrated in FIG. 6, the transceiver module 306 can contain a socket 308 for the pulse oximeter cable 904 if the pulse oximeter 902 is separate from the wrist-mounted enclosure 204. In one embodiment, the pulse oximeter 1402 is in the wrist strap, as illustrated in FIG. 14, so no separate device on the finger is necessary.

In one embodiment, the Remote Monitoring Device is configured as a ring-shaped device that can be attached around a body part, such as, but not limited to, a wrist, ankle, or waist, and includes a flexible circuit board, processor coupled to a Bluetooth transmitter, and a pule oximeter. The ring form of the Remote Monitoring Device can have a relay transceiver for receiving signals from the Bluetooth transmitter and for relaying those signals to the Base Station. The relay transceiver can be mounted on a Wearer or it can be mounted to a fixed location within the Wearer's cell or room.

The Remote Monitoring Device should have a ruggedized design such that it is resistant to intentional tampering and inadvertent damage, but its wrist-mounted components can be light and weigh no more than 250 grams. The Remote Monitoring Device enclosure can be constructed using polycarbonate, carbon-fiber, or other plastic material of similar strength, and the Remote Monitoring Device wrist strap can be constructed using polyurethane rubber or other material resistant to tearing and with high tensile strength.

In one embodiment, the Remote Monitoring Device contains a pulse oximeter 902, 1402 that contains an adhesive material that prevents rubbing or chafing of the components against the skin and can provide disposable adhesive sensor cable cover-ups in order to minimize the risk of hand or wrist injury during normal use. The pulse oximeter 902, 1402 can have a cable 904 that is at least 8 inches long. The cable 904 transmits $SpO_2$ and pulse rate data to the transceiver module 306 on the Remote Monitoring Device. The Remote Monitoring Device can display a human-readable serial number label, which can be visible while the Remote Monitoring Device is mounted and secured to the wrist strap.

The Remote Monitoring Device can conform to fluid ingress rating of IPX6, can operate over an ambient temperature range of 0 to 40 degrees Celsius, will not be degraded by indefinite storage at ambient temperatures ranging from −20 to +80 degrees Celsius, and can be materially compatible with cleaning solutions of up to 90% isopropyl alcohol or 10% chlorine bleach. No part of the Remote Monitoring Device that directly contacts a Wearer's skin will exceed 38 degrees Celsius.

Figure 2:
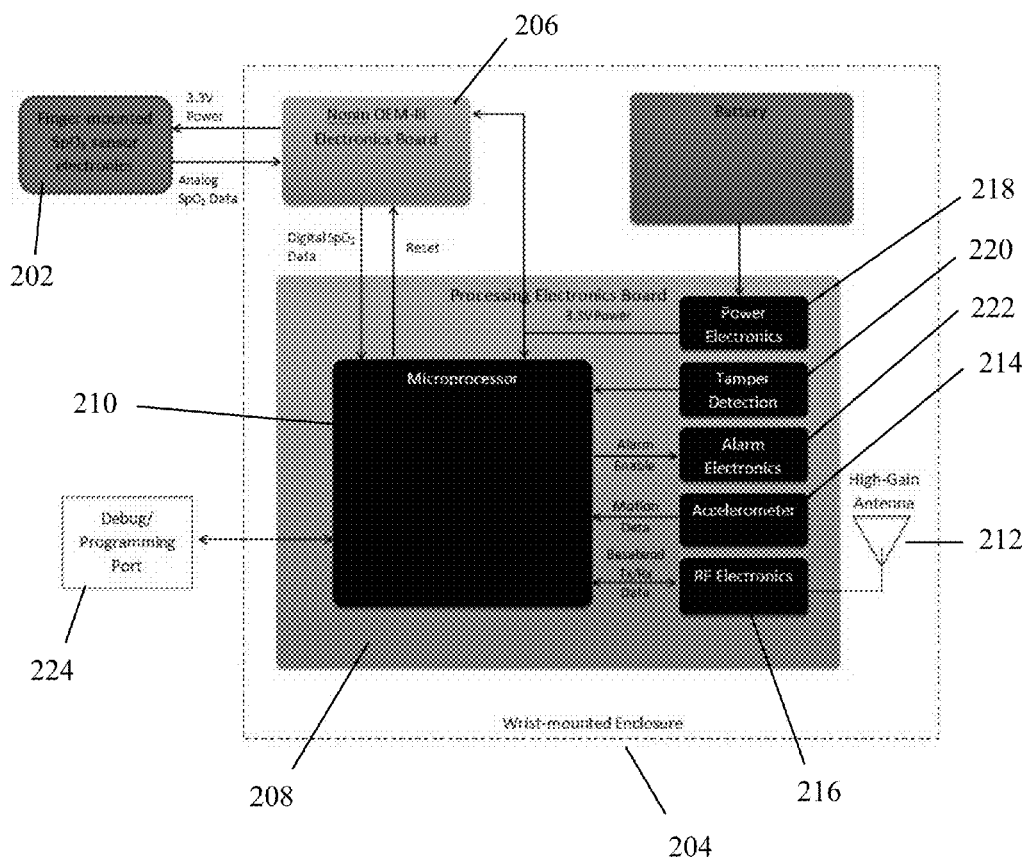
FIG. 2 is a block diagram of exemplar circuitry for a remote monitoring device.
Figure 3:
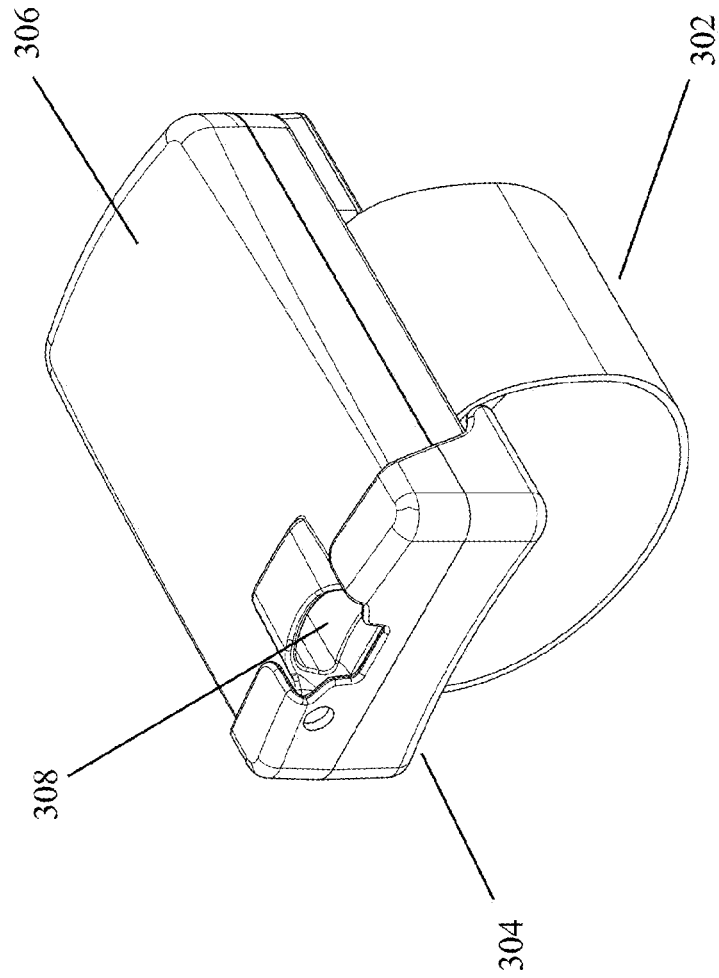
FIG. 3 illustrates a perspective top view of a remote monitoring device without a finger-based pulse oximeter attached.
Figure 4:
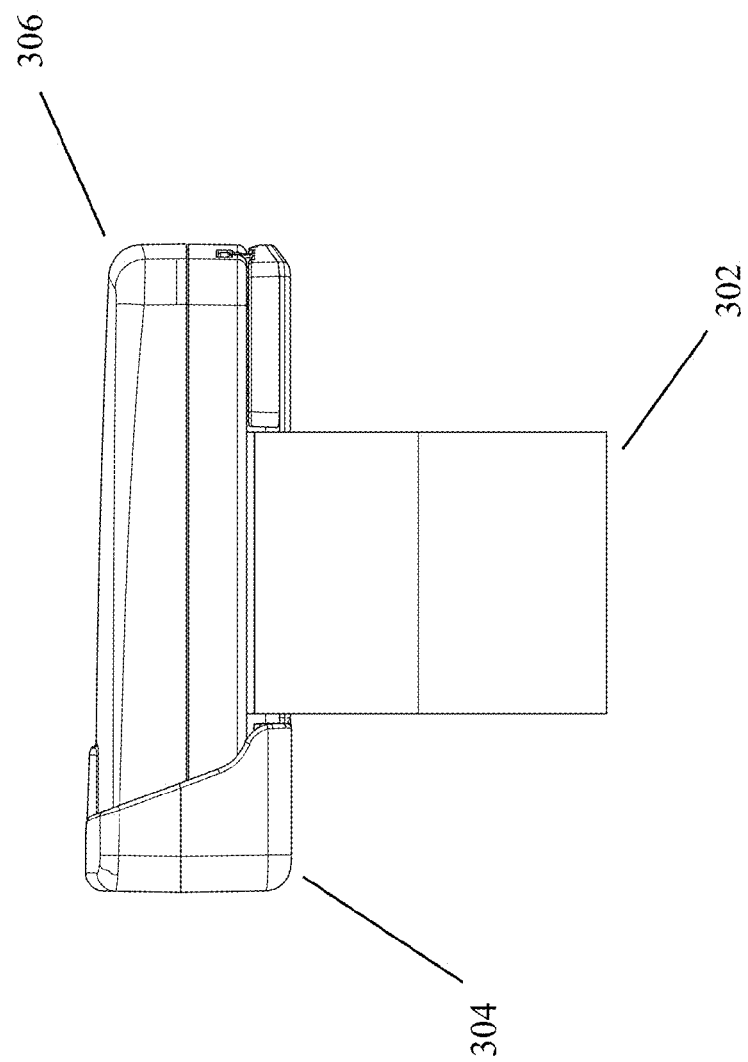
FIG. 4 illustrates a side view of a remote monitoring device without a finger-based pulse oximeter attached.
Figure 5:
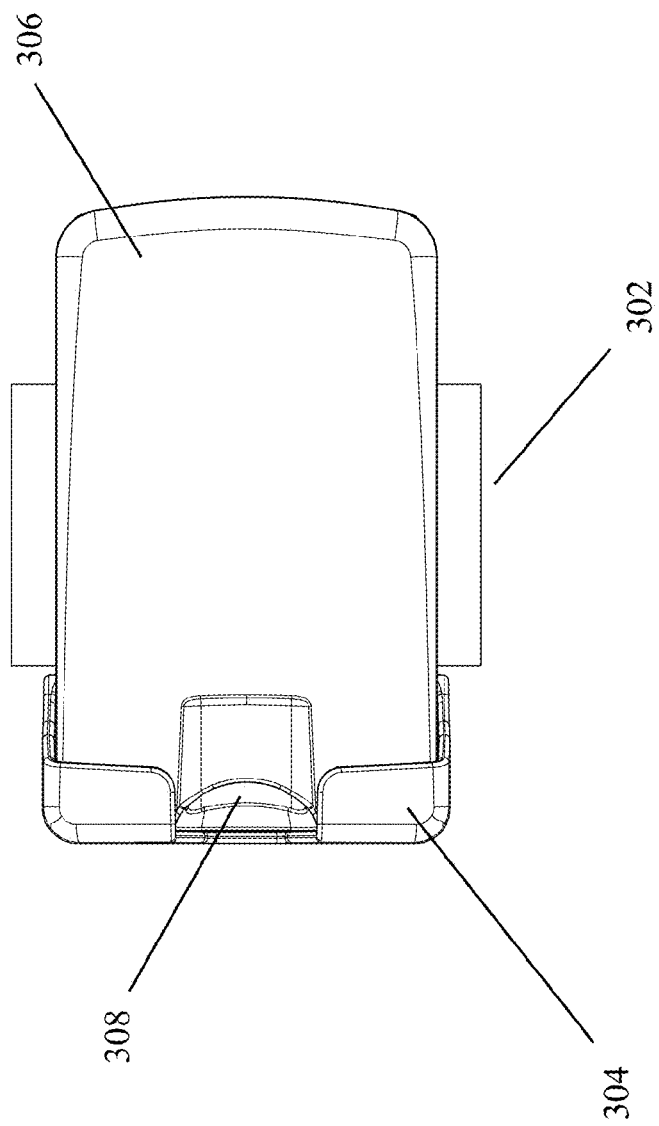
FIG. 5 illustrates a top view of a remote monitoring device without a finger-based pulse oximeter attached.

The circuitry of the Remote Monitoring Device is illustrated in FIG. 2. The pulse oximeter 902, 1402 contains $SpO_2$ sensor electronics 202, receives power from the wrist-mounted enclosure 204, and sends SpO2 analog data to the wrist-mounted enclosure 204. The circuitry in the wrist-mounted enclosure 204 includes a pulse oximeter electronics board 206 and a processing electronics board 208. The pulse oximeter electronics board 206 sends digital $SpO_2$ data to the microprocessor 210, which sends reset data to the pulse oximeter electronics board 206. The wrist-mounted enclosure 204 also contains a battery, a high-gain antenna 212 and an accelerometer 214. The high-gain antenna 212 is connected to the RF electronics 216 circuitry. The accelerometer 214 can send information to the microprocessor 210. Within the processing electronics board 208, there can be circuitry for a microprocessor 210, power electronics 218, tamper detection 220, alarm electronics 222, and RF electronics 216. The power electronics 218 can receive information from the battery and can send information to the pulse oximeter electronics board 206 and the microprocessor 210. The tamper detection 220 can send information to the microprocessor 210. The alarm electronics 222 can receive information from the microprocessor 210. The RF electronics 216 can send and receive baseband Tx/Rx Data to and from the microprocessor 210. The microprocessor 210 can send and receive information to a debug/programming port 224.

The Remote Monitoring Device can optically measure the blood oxygen saturation ($SpO_2$) of the wearer with an accuracy of 1% or better using dominant wavelengths of 660 nm±10 nm and 910±10 nm. The Remote Monitoring Device can also measure the heart rate of the wearer with an accuracy of 3 beats-per-minute (BPM) or better and can detect acceleration between 0 and ±3 Gs in any direction.

In one embodiment, the Remote Monitoring Device is capable of generating an audible alarm. The alarm may have a sound pressure level of at least 90 dBA at a distance of 10 cm and can alternate in frequency between 500 Hz and 3.5 KHz. The Remote Monitoring Device can also provide an LED indicator capable of illuminating with red, green or amber color.

The Remote Monitoring Device can communicate in various ways. In one embodiment, it has an interface to load or upgrade the device firmware and to load the Remote Monitoring Device's unique ID number. In one embodiment, it can participate in a wireless communication network and can measure the received signal strength of wireless signals received from the Base Station. The Remote Monitoring Device may detect loss of communication with the Base Station.

The Remote Monitoring Device can communicate in other pathways, including the following: (i) locking ring module communicating to fixed relay system, (ii) locking ring module communication to releasable fixed relay system on body, (iii) locking ring wirelessly communicating to cell station and satellites, (iv) adhesive film that communicates wirelessly to a fixed or body relay system.

The system receiving the relay, for purposes of providing information known to be indicative of acute behavior changes, can utilize: a visual screen, audible tones, video pictures, motion, charts, graphs, holographic projection and meters. This set of communication tools could provide greater reliability and easier data interpretation by remote monitor users. The system may also include spoken word translation of interpretive data into other languages.

The standard unit is designed to monitor and communicate oxygen levels and pulse to a remote station that can evaluate for problem conditions. However, in another embodiment, the unit can include ability for the wearer or monitoring party to communicate via the relay system to each other (via text, audio, video, motion, light display, etc.). Or such communication could be one-way. For example, the remote monitoring party can access a live video feed of the monitored party (whether through the monitoring device or through a separate but linked video system).

The system can also be configured to transmit to one single place that conducts remote monitoring and then send notification of an incident to a predetermined group or individuals for response (for example, via text message or other alert).

The Remote Monitoring Device can permanently store a 32-bit, non-volatile, unique device ID number that can be restricted from modification after it is provisioned. The Remote Monitoring Device can retrieve $SpO_2$ measurements from its pulse oximeter at least once per second and pulse rate measurements from its pulse oximeter at least once per second. The Remote Monitoring Device can retrieve acceleration measurements from its acceleration sensor at least once per second.

Wearer motion is detected by a 3-axis accelerometer in the Remote Monitoring Device unit. The raw accelerometer data is smoothed and averaged and sent to the Base Station as part of the periodic status updates. The Base Station application monitors the received accelerometer information and enters alert status if the received value falls below a user-specified threshold for a user-specified amount of time.

In an exemplary embodiment, the accelerometer in the Remote Monitoring Device runs continuously, measuring the absolute acceleration in three orthogonal axes (X, Y, and Z) approximately 5 times per second. Once per second, the Remote Monitoring Device processor reads the most recent absolute X, Y, and Z acceleration values from the accelerometer (X_Raw, Y_Raw, Z_Raw). The Remote Monitoring Device processor calculates the absolute value of the change in acceleration for each axis from the previous second (X_Delta, Y_Delta, Z_Delta). The previous value for each axis is initially set to 0 when the Remote Monitoring Device is first powered on. This delta operation nullifies the constant gravitational acceleration.

Continuing in the same example, if any of the computed delta values is smaller than a specified noise floor of approximately 16 milli-G, then that value is set to 0. The Remote Monitoring Device processor calculates the Root Mean Square (RMS) magnitude of the three acceleration values: RMSDelta=square_root (X_Delta2+Y_Delta2+Z_Delta). It then uses an exponential infinite impulse response filter to compute a running average of the RMSDelta acceleration: AvgDelta=RMSDelta*FILTER_FACTOR+AvgDelta*(1−FILTER_FACTOR). The FILTER_FACTOR used depends on whether RMSDelta is less than or greater than the current AvgDelta: If RMSDelta≥AvgDelta, FILTER_FACTOR=0.97, else FILTER_FACTOR=0.03.

When the Base Station sends a STATUS_REQUEST message to the Remote Monitoring Device, the Remote Monitoring Device processor includes the current AvgDelta as the motion value in the STATUS_RESPONSE message to the Base Station, and resets the AvgDelta value to 0. Thus, the Base Station receives a filtered value representing a weighted average magnitude of acceleration since the previous STATUS_REQUEST.

When the Base Station receives a STATUS_RESPONSE message, it compares the received motion value to a user-configured threshold (e.g., 50 milli-G). If the motion value for a wearer is below the threshold, a motion flag is set. If the value is above the threshold, the flag is cleared. If a wearer's motion flag remains set for a user-configured time (e.g., 5 minutes), the Base Station puts that Wearer in the low motion alert state.

Some embodiments implement the alarm on the Remote Monitoring Device and others implement the alarm in the Base Station. The alarm could also be implemented on both the Remote Monitoring Device and the Base Station. Regardless of implementation location, each Wearer is given baseline vital signs and the algorithm for each vital sign creating a warning is as follows: will alarm when no motion is detected and the pulse exceeds 125% of resting pulse for 30 seconds; will alarm when no motion is detected and the pulse is 70% of resting pulse for 30 seconds; will alarm when blood oxygen level is 80% of the baseline reading.

Each Remote Monitoring Device is associated with a unique identifier that is stored on the device and in the database along with biometric authentication data such as, but not limited to, fingerprint, facial photograph, iris, etc.

Upon application of power, the Remote Monitoring Device will be inactive and will verify the integrity of its internal firmware. When the Base Station has deactivated the Remote Monitoring Device, the software can place all sensors in their low-power/standby modes.

The Remote Monitoring Device can communicate in various ways. When communicating, it can detect the presence of up to 3 bit errors in received data. Some of the data objects the Remote Monitoring Device can communicate to the Base Station via the wireless network include, but are not limited to, device ID number, device pulse oximeter status, wearer's current $SpO_2$, Wearer's current pulse rate, Wearer's current level of physical activity, device current battery state of charge, device current tamper switch activation state, and wireless network most-recent received signal strength value. During normal use (i.e., non-alert/alarm), the Remote Monitoring Device may transmit data to the Base Station at 10-second intervals+/−100 ms. During an alert/alarm event, the Remote Monitoring Device can transmit data to the Base Station at 1-second intervals+/−100 ms.

The Remote Monitoring Device can receive the following commands from the Base Station: activate; deactivate; alarm; chirp; and silence. Following receipt of an "Activate" command from the Base Station, the Remote Monitoring Device can perform required measurement and data communication functions. Following receipt of a "De-Activate" command from the Base Station, the Remote Monitoring Device will cease performing measurement and data communication functions. Following receipt of an "Alarm" command from the Base Station, the Remote Monitoring Device can emit a constant audible alarm. Following receipt of a "Chirp" command from the Base Station, the Remote Monitoring Device can emit an intermittent audible "chirp" alert at 7.9-second intervals for 100 ms. If no data is received from the Base Station for at least 10 seconds, the Remote Monitoring Device can emit an audible "chirp" alert at 7.9-second intervals for 100 ms. When the Remote Monitoring Device is not transmitting data to the Base Station, the software can place the Remote Monitoring Device radio into its low-power/standby mode.

While the exemplary systems elsewhere described allows for rapid identification of a monitored party (via the number of the Remote Monitoring Device), the monitored party may not be the typical location (cell). Rather, the party may be incapacitated in another location. Thus, in another embodiment, the Remote Monitoring Device could provide location information of the monitored party. Location could be determined through (a) WiFi or other RF-based indoor triangulation, (b) GPS, (c) proximity sensor (which sensor is the party near) or other wireless communication that allows for location verification. The location function can be enhanced with the use of a local alert or alarm (for example, on the Remote Monitoring Device) such that a caregiver could find the party by sound.

Examples of Use

This section provides brief descriptions of the use cases for various scenarios encountered in the operation of, and communication between, the Base Station and Remote Monitoring Device. Some steps in the various processes identify potential conditions for changing the state of the Remote Monitoring Device LED indicator. Not all of these states may be implemented.

In the initial system setup, the BSC and all other devices are not configured and are powered off. To start the setup, the Admin connects the BSR to the BSC USB port and powers on BSC and waits for the operating system to boot. Next, the Admin logs in to the operating system account and Admin installs and launches the disclosed software application. The Admin then configures the Admin and other user accounts. Finally, the software application begins sequencing through time slots (ex: 25 slots, nominally 800 mSec each), and, during each unassigned time slot (all at this point), the software application sends a multicast discover message searching for devices. At the end of the initial system setup, the BSC and BSR are powered on, the application is running, and no devices are activated or available for activation. FIG. 18 illustrates the information the Admin can enter when launching the disclosed software application for the first time.

In the clean system power down stage, the BSC is initially configured and powered on, and other devices are in various states. To start the power down, the user logs into the BSC and requests all active devices to enter the inactive state. However, the application remembers which devices were active. Next, the user exits the application and powers down the BSC, which, in turn, powers down the BSR. As a result of the clean system power down, the BSC is powered off and all other devices are in an inactive or off state.

When discovering a newly powered on Remote Monitoring Device, the initial conditions are that the BSC and BSR are powered on, the software application is running, at least one unassigned time slot is available, and the device being powered on may or may not already be in the BSC list of "visible" devices.

To initiate the discovery of a newly powered on Remote Monitoring Device, the user inserts a battery into the device. The device then performs POST and enters a discoverable state. If POST passes, the device enters LED_STATE1 and the device radio is on full time listening for multicast DISCOVER command or a COMMAND or STATUS_REQUEST command directed to the device's ID. If POST fails, the device enters LED_STATE2. Then, the BSC eventually sends a DISCOVER command. The device waits a random delay (50-200 mSec) and then responds with a DISCOVER_RESPONSE message. Next, the BSC receives a DISCOVER_RESPONSE message and compares the device's ID with known devices in the device list. If the device ID is not found in the list, the BSC assigns the device to the current timeslot with a requested state of Inactive. If the device ID is found in list, the BSC updates the time stamp and sets the requested device state to the state specified in the list. Next, the BSC sends a COMMAND message to the responding device, telling it (i) its requested state (inactive or active), (ii) the time to the next scheduled message (nominally 20 sec), and (iii) how long to listen for a message before declaring a host communication failure. The device then receives this COMMAND message and shuts off its radio and sleeps until just before the next scheduled message time. The device is in LED_STATE3 if it is inactive or LED_STATE4 if it is active.

Figure 26:
FIG. 26 illustrates a graphical user interface wherein an administrator can register or remove remote monitoring devices.

As a result of discovering a newly powered on Remote Monitoring Device, the device is registered in the BSC device list, as illustrated in FIG. 26, it is assigned a communication time slot, it is in the desired state, and it is in a sleep/wake cycle while waiting for the next message from the base station.

When updating the status of an active or inactive Remote Monitoring Device, the initial conditions of the system are that the BSC and BSR are powered on, the software application is running, and at least one time slot is assigned to a device with a current state of inactive or active.

To initiate the status update of an active or inactive Remote Monitoring Device, the user running the software application GUI selects an active or inactive device from the list and sets the requested state (ex: active, inactive, off). The application's time slot scheduler then comes to the time slot assigned to the inactive device, checks the obtains desired state of the device from the device list, and sends a COMMAND to the device specifying the desired state and next communication time. The device then receives the COMMAND message. If the desired state is off, the device shuts off its radio and sleeps until unlocked/locked. If the desired state is active or inactive, the device shuts off its radio and sleeps until just before the next scheduled message time. While the device is inactive, it is in LED_STATE3. While the device is active, it is in LED_STATE4. While the device is off, it is in LED_STATE0. As a result of updating the status of an active or inactive Remote Monitoring Device, the device changes to the desired state.

When obtaining the status from an active device, the initial conditions are that the BSC and BSR are powered on, the software application is running, and at least one time slot is assigned to a device with a current state of active.

To obtain the status of an active device, the device will wake up just prior to scheduled time slot and turn on its radio to listen for a message from the Base Station. At this point in time, the device is in LED_STATE5. The software application's time slot scheduler comes to the time slot assigned to the active device, sends a STATUS_REQUEST, and collects status parameters. The active device receives a STATUS_REQUEST, collects status parameters, and responds with a STATUS_RESPONSE message. Then, the software application performs assessment algorithms on the parameters, sets a local audible alarm based on the results from the algorithm, and determines the desired device state. The software application then sends a COMMAND message to the active device with the desired device state (ex: inactive, active, chirp, alarm) and the next communication time. The device then receives the COMMAND message and shuts off its radio and sleeps until just before the next scheduled message time. At this point, if the device's state is inactive, active, or chirp, it is in LED_STATE3. If the device's state is alarm, it is in LED_STATE6. As a result of obtaining the status from an active device, the device is in the desired state based on the status assessment algorithm.

When the device loses communication with the Base Station, the initial conditions are that the BSC and BSR are powered on, the software application is running, and at least one time slot is assigned to a device with a current state of active or inactive.

If the device loses communication with the Base Station, the device discovers this after it wakes up just prior to scheduled slot time, turns on its radio to listen for a message from the Base Station (device is in LED_STATE5), receives no message at the assigned time, keeps its radio on and continues to listen for a message, and takes appropriate action depending on whether the device is active or inactive. If the device is active and if no message is received within a previously specified timeout, the device puts its alarm in ALARM_STATE_NO_COMM, continues to keep its radio on and listen for a message, and, when a message is received, it silences the alarm and resumes normal operation. If the device is inactive and if no message is received within a previously specified timeout, the device enters the off state (i.e., LED_STATE0), and remains in the off state until unlocked/locked or the battery is removed/replaced. At this point, the process continues as though a newly powered on Remote Monitoring Device is being discovered.

When there is an unplanned BSC power down, the initial conditions are that the BSC and BSR are powered on, the software application is running, and at least one time slot is assigned to a device with a current state of active. If the BSC then shuts off without following the clean system power down procedure, the process continues as though the device lost communication with the Base Station for all active and inactive devices. As a result, the BSC and BSR are powered off, all previously inactive devices are off, and all active devices indicate a loss of communication.

When the system powers up, the initial conditions are that the BSC is configured, but powered off, and all other devices are in various states (off, inactive, active). To power the system up, the user powers on the BSC, which powers on the BSR, waits for the operating system to boot, and logs into the operating system account. The software application will start up automatically and restore devices to their previously saved state (i.e., active or inactive). The software application then begins sequencing through timeslots. For each unassigned time slot, the software application will send a DISCOVER multicast and, if a DISCOVER_RESPONSE is received, the software application will continue as though the process of discovering a newly powered on Remote Monitoring Device is occurring and system is at the step where the BSC compares the device ID with known devices in its list. If no response is received, the software application will continue to the next time slot. For each assigned time slot, the software application will attempt to send a STATUS_REQUEST to the device if it was previously active. If the device was previously inactive, the software application will attempt to send a COMMAND to the device. As a result, the BSR and BSR are powered on and the software application is running and trying to DISCOVER or communicate with devices.

When the Base Station software application stops running or the BSC reboots, the initial conditions are that the BSC and BSR are powered on and the software application is running If the software application quits running for any reason or if the BSC reboots or halts, the BSC and BSR remain powered on. After a time period, the BSR detects a loss of communication with the BSC and sets its audible alarm to ALARM_STATE_NO_COMM. The BSR continues to indicate loss of communication until a message is received from the BSC. At that point, the process continues for all active and inactive devices as though the device lost communication with the Base Station. When the Base Station software application stops running or the BSC reboots, the result is that the software application is not running and that the BSR and active devices are indicating a communication loss.

When the user is restarting the software application or the computer is recovering after a BSC reboot, the initial conditions are that the software application is stopped or the BSC is halted or rebooting. If the BSC is halted or rebooting, the user performs action necessary to restart the operating system and logs into the user's operating system account. The software application starts automatically. The BSR detects resumption of communication with the BSC and it silences the local alarm. At that point, the process continues as though the system is powering up and the software application is restoring a previously saved list of visible devices. As a result, the BSC and BSR are powered on, and the software application is running and trying to DISCOVER or communicate with device.

Battery Charger

In one embodiment, the Battery Charger can accept a 120 VAC/60 Hz power input, a 240 VAC/50 Hz power input, and an IEC 60230 Type C14 grounded receptacle power input. The Battery Charger can provide an interface to load or upgrade the device firmware.

The Battery Charger can charge at least six (6) Remote Monitoring Device batteries simultaneously at a constant current when the battery voltage is below the battery's constant-voltage threshold. When the battery reaches its constant-voltage threshold, the Battery Charger will switch to charging inserted batteries at a constant voltage. It will terminate battery charging when charge current drops below the battery's charge-termination current during constant-voltage charging. It can determine the state-of-charge of all inserted batteries by communicating with a gas gauge IC built into each battery pack. In one embodiment, the Battery Charger may only allow insertion of Remote Monitoring Device batteries.

The Battery Charger may provide an LED indicator for each battery-charging receptacle, wherein the LED indicators are individually capable of illuminating with red, green or amber color to indicate the status of the charge. The Battery Charger indicators can be positioned adjacent to their associated battery-charging receptacle, such that the planar distance to any other receptacle is far enough away to make it obvious that the indicator is associated with its corresponding receptacle.

Upon insertion of a battery, the Battery Charger will initiate charging of the battery, but will discontinue charging of any battery whose charge rate exceeds the maximum permissible charge rate for 2 seconds or more. Upon removal of a battery from a charging receptacle, the Battery Charger will disable charging by the associated receptacle.

Upon application of power, the Battery Charger will disable charging by all battery charging receptacles and, if batteries are inserted in any battery charging receptacles, the Battery Charger can indicate a charging error on these receptacles. Further, the Battery Charger may display a test pattern on all LEDs simultaneously by cycling all LEDs through the colors red, amber, and green for one (1) second each.

Upon removal of a battery from a charging receptacle, or if no battery is inserted in a battery charging receptacle, the Battery Charger can extinguish the LED indicator associated with that receptacle. During battery charging, the Battery Charger may illuminate the receptacle's associated LED to a constant amber color. After completion of battery charging, the Battery Charger may illuminate the receptacle's associated LED to a constant green color. If a charging error occurs, the Battery Charger may illuminate the affected receptacle's associated LED red, flashing at 1 Hz with a 50% duty cycle.

In some embodiments, the system includes localized recharging on the Remote Monitoring Device. For example, the device could be recharged through kinetic motion, body heat, or solar energy.

Figure 17:
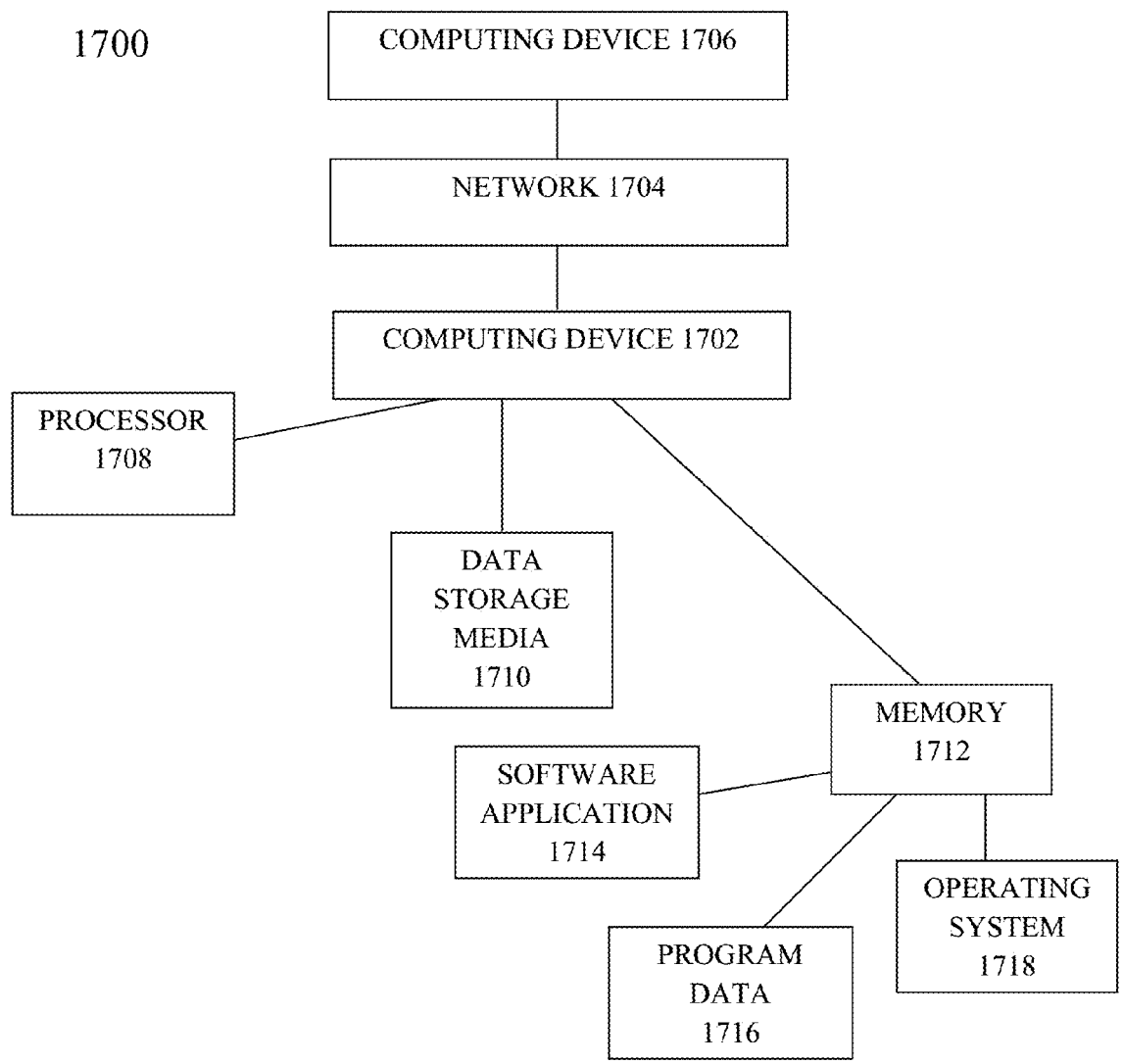
FIG. 17 is a schematic block diagram of an example computing system that may be used in accordance with one embodiment of the present invention.

The disclosed invention involves technology that uses a computing system. FIG. 17 is a schematic block diagram of an example computing system 1700. The invention includes at least one computing device 1702. In some embodiments the computing system further includes a communication network 1704 and one or more additional computing devices 1706 (such as a server).

Computing device 1702 can be, for example, located in a place of business or can be a computing device located in a prison or psychiatric ward or hospital. In some embodiments, computing device 1702 is a mobile device. Computing device 1702 can be a stand-alone computing device or a networked computing device that communicates with one or more other computing devices 1706 across a network 1704. The additional computing device(s) 1706 can be, for example, located remotely from the first computing device 1702, but configured for data communication with the first computing device 1702 across a network 1704.

In some examples, the computing devices 1702 and 1706 include at least one processor or processing unit 1708 and system memory 1712. The processor 1708 is a device configured to process a set of instructions. In some embodiments, system memory 1712 may be a component of processor 1708; in other embodiments system memory is separate from the processor. Depending on the exact configuration and type of computing device, the system memory 1712 may be volatile (such as RAM), non-volatile (such as ROM, flash memory, etc.) or some combination of the two. System memory 1712 typically includes an operating system 1718 suitable for controlling the operation of the computing device, such as the Linux operating system. The system memory 1712 may also include one or more software applications 1714 and may include program data 1716.

The computing device may have additional features or functionality. For example, the device may also include additional data storage devices 1710 (removable and/or non-removable) such as, for example, magnetic disks, optical disks, or tape. Computer storage media 1710 may include volatile and nonvolatile, removable and non-removable media implemented in any method or technology for storage of information, such as computer readable instructions, data structures, program modules, or other data. System memory, removable storage, and non-removable storage are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing device. An example of computer storage media is non-transitory media.

In some examples, one or more of the computing devices 1702, 1706 can be located in a confinement institution. In other examples, the computing device can be a personal computing device that is networked to allow the user to access the present invention at a remote location, such as in a user's home, office or other location. In some embodiments, the computing device 1702 is a smart phone, tablet, laptop computer, personal digital assistant, or other mobile computing device. In some embodiments the invention is stored as data instructions for a smart phone application. A network 1704 facilitates communication between the computing device 1702 and one or more servers, such as an additional computing device 1706, that host the system. The network 1704 may be a wide variety of different types of electronic communication networks. For example, the network may be a wide-area network, such as the Internet, a local-area network, a metropolitan-area network, or another type of electronic communication network. The network may include wired and/or wireless data links. A variety of communications protocols may be used in the network including, but not limited to, Wi-Fi, Ethernet, Transport Control Protocol (TCP), Internet Protocol (IP), Hypertext Transfer Protocol (HTTP), SOAP, remote procedure call protocols, and/or other types of communications protocols.

In some examples, the additional computing device 1706 is a Web server. In this example, the first computing device 1702 includes a Web browser that communicates with the Web server to request and retrieve data. The data is then displayed to the user, such as by using a Web browser software application. In some embodiments, the various operations, methods, and rules disclosed herein are implemented by instructions stored in memory. When the instructions are executed by the processor of one or more of the computing devices 1702 and 1706, the instructions cause the processor to perform one or more of the operations or methods disclosed herein. Examples of operations include sending and receiving messages to and from a Remote Monitoring Device; performing assessment algorithms on collected Wearer data; sending an action command to a Remote Monitoring Device; and other operations.

The various embodiments described above are provided by way of illustration only and should not be construed to limit the claims attached hereto. Those skilled in the art will readily recognize various modifications and changes that may be made without following the example embodiments and applications illustrated and described herein and without departing from the true spirit and scope of the following claims.

We claim:

1. An apparatus comprising a wearable device, wherein the wearable device includes:
   a circuit-board enclosure having a cradle containing a removable battery, wherein the cradle is in engagement with a transceiver module for contacting a wrist of a person;
   an adjustable strap for encircling the wrist and removably attaching the wearable device to the wrist, the adjustable strap having a first and a second portion sandwiched between a portion of the transceiver module and a portion of the cradle, with one of the adjustable strap portion being an end of the adjustable strap;
   a pulse oximeter for sensing change in a blood-related parameter;
   an accelerometer for sensing change in a body movement of the person; and
   a transmitter for transmitting the blood-related parameter and the body movement.

2. The apparatus of claim 1, wherein the pulse oximeter is a finger-mountable pulse oximeter.

3. The apparatus of claim 1, wherein the pulse oximeter is located on the inside of the adjustable strap.

4. The apparatus of claim 1, wherein the wearable device is also securably attachable to the person.

5. The apparatus of claim 1, further comprising a base station for bidirectional wireless communication with the wearable device.

6. The apparatus of claim 5, wherein biometric information for the person experiencing an emergency medical condition is inputted into the base station.

7. The apparatus of claim 6, wherein the biometric information inputted into the base station is baseline pulse data for use in determining whether the person is experiencing an emergency medical condition.

8. The apparatus of claim 1, wherein the adjustable strap encirlces a finger and includes a flexible circuit board supporting a processor coupled to a Bluetooth transmitter and the pulse-oximeter.

9. The apparatus of claim 8, further comprising a relay transceiver for receiving signals from the Bluetooth transmitter and relaying them to a base station.

10. The apparatus of claim 9, wherein the relay transceiver is mountable to the person or to a fixed location within a space containing the person.

* * * * *